United States Patent
Leger et al.

(10) Patent No.: US 6,204,279 B1
(45) Date of Patent: *Mar. 20, 2001

(54) PEPTIDOMIMETIC EFFLUX PUMP INHIBITORS

(75) Inventors: Roger Leger, Mountain View; Ving J. Lee, Los Altos; Miles She, Oakland, all of CA (US)

(73) Assignee: Microcide Pharmaceuticals, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/089,734

(22) Filed: Jun. 3, 1998

(51) Int. Cl.$^7$ .................. A61K 31/42; C07D 263/52; C07D 413/00

(52) U.S. Cl. .................. 514/375; 514/374; 548/215; 548/217

(58) Field of Search .................. 514/212, 227.8, 514/228.2, 231.5, 233.5, 235.2, 235.8, 236.5, 236.8, 252, 253, 336, 337, 339, 340–343, 365, 374, 375, 383, 397, 406, 414, 422, 438, 443, 444, 469, 471; 540/524; 544/58.4, 132–133, 137, 139–141, 146, 152–3, 369, 370, 372, 373, 376, 379; 546/269, 273–6, 278–284; 548/204, 231, 236, 266.2, 266.4, 266.6, 267.6, 336, 343, 344, 374, 378, 468, 517–8, 525, 527, 561, 215, 217; 549/58–60, 76, 407, 496

(56) References Cited

U.S. PATENT DOCUMENTS

| | | | |
|---|---|---|---|
| 5,104,869 | * 4/1992 | Albright et al. | 514/212 |
| 5,811,424 | * 9/1998 | Shibata et al. | |
| 5,981,528 | * 11/1999 | Gravestock | 514/252 |
| 5,989,832 | * 11/1999 | Trias et al. | 435/7.2 |

FOREIGN PATENT DOCUMENTS

| | | |
|---|---|---|
| 078 703 | * 5/1983 | (EP) . |
| 280 610 | * 8/1988 | (EP) . |
| 0 280 610 | 8/1988 | (EP) . |
| 365 956 | * 5/1990 | (EP) . |
| 624 377 | * 11/1994 | (EP) . |
| 2085447 | * 4/1982 | (GB) . |
| 2272441 | * 5/1994 | (GB) . |
| 09323984 | * 12/1997 | (JP) . |
| 96/33285 | 10/1996 | (WO) . |
| 96/40738 | * 12/1996 | (WO) . |
| 96/40743 | * 12/1996 | (WO) . |
| 97/34923 | * 9/1997 | (WO) . |
| 97/40066 | * 10/1997 | (WO) . |

OTHER PUBLICATIONS

Lorian (editor), "Laboratory Methods Used to Assess the Activity of Antimicrobial Combinations," in *Antibiotics in Laboratory Medicine*, Fourth Edition, Williams & Wilkins, pp. 333–338 (1996).

Malouin et al., "Outer Membrane and Porin Characteristics of *Serratia marcescens* Grown In Vitro and in Rat Intraperitoneal Diffusion Chambers," *Infection and Immunity* 58:1247–1253 (1990).

Murray, "Can Antibiotic Resistance be Controlled?" *New Engl. J. Med.* 330:1229–1230 (1994).

NCCLS publication entitled "Methods for Dilution Antimicrobial Susceptibility Test for Bacteria that Grow Aerobically—Fourth Edition: Approved Standard," NCCLS Document M7–A4, vol. 17, No. 2 (1997).

Nikaido, "Prevention of Drug Access to Bacterial Targets: Permeability Barriers and Active Efflux," *Science* 264:382–388 (1994).

Ocain and Rich, "Synthesis of Sulfur–Containing Analogues of Bestatin. Inhibition of Aminopeptidases by α–Thiolbestatin Analogues," *J. Med. Chem.* 31:2193–2199 (1988).

Reitz et al., "The Biochemical Mechanisms of Resistance by Streptococci to the Antibiotics D–Cycloserine and O–Carbamyl–D–Serine," *Biochem. J.* 6:2561–2570 (1967).

Santoro and Levison, "Rat Model of Experimental Endocarditis," *Infection and Immunity* 19:915–918 (1978).

Sato et al., "Antimicrobial Activity of DU–6859, a New Potent Fluoroquinolone, against Clinical Isolates," *Antimicrobial Agents and Chemotherapy* 36:1491–1498 (1992).

Seoane and Levy, "Reversal of MarR binding to the regulatory region of the *marRAB* operon by structurally unrelated inducers," *Abstr. of the Am. Soc. for Microbiol. Gen. Meeting*, Las Vegas, NV Abstract H–26 (1994).

Speer et al., "Bacterial Resistance to Tetracycline: Mechanisms, Transfer, and Clinical Significance," *Clin. Microbiol. Reviews* 5:387–399 (1992).

Spratt, "Resistance to Antibiotics Mediated by Target Alterations," *Science* 264:388–393 (1994).

Tamura et al., "Rational Design, Synthesis, and Serine Proteases Inhibitory Activity of Novel P1–Argininoyl Heterocycles," *Bioorganic & Medicinal Chemistry Letters* 7:1359–1364 (1997).

Tanaka et al., "Antimicrobial Activity of DV–7751a, a New Fluoroquinolone," *Antimicrobial Agents and Chemotherapy* 37:2112–2218 (1993).

Vogelman et al., "In Vivo Postantibiotic Effect in a Thigh Infection in Neutropenic Mice," *Journal of Infectious Diseases* 157:287–298 (1988).

Ahmed et al., "A Protein That Activates Expression of a Multidrug Efflux Transporter upon Binding the Transporter Substrates," *J. Biol. Chem.* 269:28506–28513 (1994).

Bergeron, "A Review of Models for the Therapy of Experimental Infections," *Scand. J. Infect Dis. Suppl.* 14:189–206 (1978).

(List continued on next page.)

*Primary Examiner*—Howard C. Lee
(74) *Attorney, Agent, or Firm*—Lyon & Lyon LLP

(57) ABSTRACT

Compounds are described which have efflux pump inhibitor activity. Also described are methods of using such efflux pump inhibitor compounds and pharmaceutical compositions which include such compounds.

22 Claims, No Drawings

OTHER PUBLICATIONS

Davis, "Activity of Gentamicin, Tobramycin, Polymyxin B, and Colistimethate in Mouse Protection Tests with *Pseudomonas aeruginosa*," *Antimicrobial Agents and Chemotherapy* 8:50–53 (1975).

Day et al., "A simple method for the study in vivo of bacterial growth and accompanying host response," *Journal of Infection* 2:39–51 (1980).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Gordon et al., "Design of Novel Inhibitors of Aminiopeptidases. Synthesis of Peptide–Derived Diamino Thiols and Sulfur Replacement Analogues of Bestatin," *J. Med. Chem.* 31:2199–2211 (1988).

Kelly et al., "Surface Characteristics of *Pseudomonas aeruginosa* Grown in a Chamber Implant Model in Mice and Rats," *Infection and Immunity* 57:344–350 (1989).

Larock, "Ch. 8—Lactone and Lactam Formation," *Comprehensive Organic Transformations: A Guide to Functional Group Preparations*, VCH Publishers, pp. 941–962 (1992).

* cited by examiner

PEPTIDOMIMETIC EFFLUX PUMP INHIBITORS

FIELD OF THE INVENTION

This invention relates to the field of antimicrobial agents and to methods for identification and characterization of potential antimicrobial agents. More particularly, this invention relates to antimicrobial agents for which the mode of action involves cellular efflux pumps and the regulation of efflux pumps.

BACKGROUND

The following background material is not admitted to be prior art to the pending claims, but is provided only to aid the understanding of the reader.

Antibiotics have been effective tools in the treatment of infectious diseases during the last half century. From the development of antibiotic therapy to the late 1980s there was almost complete control over bacterial infections in developed countries. The emergence of resistant bacteria, especially during the late 1980s and early 1990s, is changing this situation. The increase in antibiotic resistant strains has been particularly common in major hospitals and care centers. The consequences of the increase in resistant strains include higher morbidity and mortality, longer patient hospitalization, and an increase in treatment costs. (B. Murray, 1994, *New Engl. J. Med.* 330: 1229–1230.)

The constant use of antibiotics in the hospital environment has selected bacterial populations that are resistant to many antibiotics. These populations include opportunistic pathogens that may not be strongly virulent but that are intrinsically resistant to a number of antibiotics. Such bacteria often infect debilitated or immunocompromised patients. The emerging resistant populations also include strains of bacterial species that are well known pathogens, which previously were susceptible to antibiotics. The newly acquired resistance is generally due to DNA mutations, or to resistance plasmids (R plasmids) or resistance-conferring transposons transferred from another organism. Infections by either type of bacterial population, naturally resistant opportunistic pathogens or antibiotic-resistant pathogenic bacteria, are difficult to treat with current antibiotics. New antibiotic molecules which can override the mechanisms of resistance are needed.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target (B. G. Spratt, *Science* 264:388 (1994)). There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics which would otherwise inhibit or kill the bacterial cells. Some bacteria utilize both mechanisms, combining a low permeability of the cell wall (including membranes) with an active efflux of antibiotics. (H. Nikaido, *Science* 264:382–388 (1994)).

In some cases, antibiotic resistance due to low permeability is related to the structure of the bacterial membranes. In general, bacteria can be divided into two major groups based on the structure of the membranes surrounding the cytoplasm. Gram-positive (G+) bacteria have one membrane, a cytoplasmic membrane. In contrast, Gram-negative (G−) bacteria have two membranes, a cytoplasmic membrane and an outer membrane. These bacterial membranes are lipid bilayers which contain proteins and may be associated with other molecules. The permeability of bacterial membranes affects susceptibility/resistance to antibiotics because, while there are a few molecular targets of antibiotics, e.g. penicillin-binding proteins, that are accessible from the outer leaflet of the cytoplasmic membranes, the principal targets for antibiotics are in the cytoplasm or in the inner leaflet of the cytoplasmic membrane. Therefore for an antibiotic which has a target in the cytoplasmic membrane, in Gram-negative bacteria that antibiotic will first need to cross the outer membrane. For a target in the cytoplasm, an antibiotic will need to cross the cytoplasmic membrane in Gram-positive bacteria, and both the outer and cytoplasmic membranes in Gram-negative bacteria. For both membranes, an antibiotic may diffuse through the membrane, or may cross using a membrane trasport system.

For Gram-negative bacteria, the lipid composition of the outer membrane constitutes a significant permeability barrier. The outer layer of this outer membrane contains a lipid, lipopolysaccharide (LPS), which is only found in the outer membrane of Gram-negative bacteria The lipid layer of the outer membrane is highly organized in a quasi-crystalline fashion and has a very low fluidity. Because of the low fluidity of the lipid layer of the outer membrane, even lipophilic antibiotics will not diffuse rapidly through the lipid layer. This has been shown experimentally, hydrophobic probe molecules have been shown to partition poorly into the hydrophobic portion of LPS and to permeate across the outer membrane bilayer at about one-fiftieth to one-hundredth the rate through the usual phospholipid bilayers (like the cytoplasmic membrane bilayer).

Some antibiotics may permeate through water-filled porin channels or through specific transport systems. Many of the porin channels, however, provide only narrow diameter channels which do not allow efficient diffusion of the larger antibiotic molecules. In addition, many porin channels are highly hydrophilic environments, and so do not efficiently allow the passage of hydrophobic molecules. Thus, the outer membrane acts as a molecular sieve for small molecules. This explains, in part, why Gram-negative bacteria are generally less susceptible to antibiotics than Gram-positive bacteria, and why Gram-negative bacteria are generally more resistant to large antibiotics, such as glycopeptides, that cannot cross the outer membrane.

The cytoplasmic membrane also provides a diffusion barrier for some antibiotics. However, since the fluidity of the lipid layer of the cytoplasmic membrane is higher than that of the outer membrane of Gram-negative bacteria, drugs that show some lipophilicity will be able to permeate through the lipid layer. Other drugs, such as phosphonomycin or D-cycloserine that have very low solubility in a lipophilic environment will cross the cytoplasmic membrane by using a transport system. In this case, though, if the transport system is not synthesized, the bacteria will become resistant to the drug (Peitz et al., 1967, *Biochem. J.* 6: 2561).

Decreasing the permeability of the outer membrane, by reducing either the number of porins or by reducing the number of a certain porin species, can decrease the susceptibility of a strain to a wide range of antibiotics due to the decreased rate of entry of the antibiotics into the cells. However, for most antibiotics, the half-equilibration times are sufficiently short that the antibiotic could exert its effect unless another mechanism is present. Efflux pumps are an example of such other mechanism. Once in the cytoplasm or periplasm a drug can be transported back to the outer medium. This transport is mediated by efflux pumps, which are constituted of proteins. Different pumps can efflux specifically a drug or group of drugs, such as the NorA system that transports quinolones, or Tet A that transports tetracyclines, or they can efflux a large variety of molecules, such as certain efflux pumps of *Pseudomonas aernginosa*. In general, efflux pumps have a cytoplasmic component and energy is required to transport molecules out of the cell. Some efflux pumps have a second cytoplasmic membrane protein that extends into the periplasm. At least some efflux pumps of *P. aeruginosa* have a third protein located in the outer membrane.

Efflux pumps are involved in antibiotic resistance since, in some cases, they can remove a significant fraction of the antibiotic molecules which manage to enter the cells, thereby maintaining a very low intracellular antibiotic concentration. To illustrate, *P. aeruginosa* laboratoryerived mutant strain 799/61, which does not produce any measurable amounts of efflux pump is 8 to 10 fold more susceptible to tetracycline and ciprofloxacin than the parent strain *P. aeruginosa* 799, which synthesizes efflux pumps. Also, null mutants of mexA, the cytoplasmic component of a *P. aeruginosa* efflux pump, are more susceptible to antibiotics than the wild type.

The physiological role of efflux pumps has not been clearly defined yet. They are involved in drug resistance but they also are involved in the normal physiology of the bacterial cell. The efflux pump coded in the mexA operon of *P. aeruginosa* has been shown to be regulated by the iron content of the medium, and it is co-regulated with the synthesis of the receptors of siderophores. Siderophores are molecules that are needed for bacterial growth under iron starvation conditions, such as during infection of an animal. They are synthesized in the cytoplasm and exported when the bacterial cell needs iron. Siderophores scavenge iron within the infected animal and return the iron to the microbe to be used for essential microbial processes. Since there is essentially no free iron in the bodies of animals, including the human body, the production of siderophores by infecting bacteria is an important virulence factor for the progress of the infection.

Even organisms normally surrounded by a cell envelope of relatively high permeability can develop resistance by decreasing the permeability of the envelope. When an agent mainly diffuses across the barrier through a specific channel, mutational loss of the channel can be an efficient mechanism for resistance. A "nonclassical" beta-lactam compound, imipenem, shows an exceptional activity against *P. aeruginosa*, mainly because this agent diffuses though a specific channel, OprD, whose physiological finction appears to be that of the transport of basic amino acids. However, *P. aeruginosa* could become resistant to imipenem by simply losing the oprD channel, and currently a large fraction of *P. aeruginosa* strains isolated from the hospital environment are resistant as a result of this modification. In a similar manner, beta-lactam compounds designed to mimic iron-chelating compounds (siderophores) during their transport through the outer membranes are known to select mutants that are defective in the specific transport of these siderophores.

In summary, the above discussion indicates that cellular factors affecting transport (both active and passive transport) of antibiotics into bacterial cells are important components of antibiotic resistance for many bacterial species.

SUMMARY

This invention concerns particular compounds which are efflux pump inhibitors, and which are therefore compounds which inhibit cellular efflux pumps of bacteria or other microbes. Such efflux pumps export substrate molecules from the cytoplasm in an energy-dependent manner, and the exported substrate molecules can include antibacterial agents. Such efflux pump inhibitors are useful, for example, for treating microbial infections by reducing the export of a co-administered antimicrobial agent or by preventing the export of a compound synthesized by microbes (e.g., bacteria) to allow or improve their growth. An example of reducing the export of such a compound is inhibiting iron availability for the microbe by reducing the export of siderophores. Thus, this invention also provides compositions which include such efflux plump inhibitors and methods for treating microbial infections using those compositions.

The identification and use of efflux pump inhibitors is described in co-pending United States patent applications, Trias et al., EFFLUX PUMP INHIBITORS, Appl. No. 08/427,088, filed Apr. 21, 1995, now U.S. Pat. No. 5,989, 832, and Trias et al., EFFLUX PUMP INHIBITORS, Appl. No. not yet assigned, filed Jul. 22, 1997, and Trias et al., International Application No. PCT/US96/05469, International Publication No. WO 96/33285, entitled EFFLUX PLMP INHIBITORS, all of which are hereby incorporated by reference in their entireties including drawings. Screening methods described therein were used to identity efflux inhibitor compounds. Rational drug-design techniques were employed to afford the structures of this present invention.

The efflux pump inhibitors of the present invention have structures that are shown by the generic structures 1 or 2 below:

Structure 1

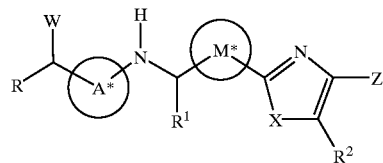

Structure 2

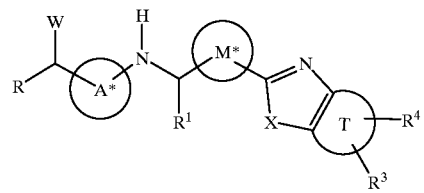

where
A*=carbonyl, CH(OH)CH$_2$
M*=(CH$_2$)$_n$(n=0, 1, or 2), CH(OH) (R- or S-configuration)
X=CH, NR*, O, S (R*=H, lower alkyl, arylalkyl)
R=H, lower alkyl, branched alkyl, fluoroalkyl, carboxyalkyl, hydroxyalkyl, aryl, 2-(or 3-)thienyl, 2-(or 3-)furyl, 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)

$NR^bR^c$, $(CH_2)_nN=CNR^bR^c$(n=0, 1, 2, 3, or 4); $R^a$ ($R^b$ or $R^c$)=H, lower alkyl, phenyl, substituted phenyl, benzyl, cyano, hydroxyl, or nitro. Alternatively $R^a+R^b$ (or $R^b+R^c$)= $(CH_2)_{2-3}$ or —CH=CH—;

$R^1$=H, lower alkyl, branched alkyl, fluoroalkyl, carboxyalkyl, hydroxyalkyl, aryl, 2-(or 3-)thienyl, 2-(or 3-)furyl, 2-(3- or 4-)pyridyl, arylalkyl, thienylalkyl, furylalkyl, pyridylalkyl, $(CH_2)_nNR^bR^c$, $(CH_2)_nNHC=$ $(NR^a)NR^bR^c$, $(CH_2)_nSC=(NR^a)NR^bR^c$, $(CH_2)_nC=(NR^a)NR^bR^c$, $(CH_2)_nN=CNR^bR^c$ (n=0, 1, 2, 3, or 4); $R^a$ ($R^b$ or $R^c$)=H, lower alkyl, phenyl, substituted phenyl, benzyl, cyano, hydroxyl, or nitro; alternatively $R^a+R^b$ (or $R^b+R^c$)= $(CH_2)_{2-3}$ or —CH=CH—;

R=H, lower alkyl, branched alkyl;

$R^3$=H, lower alkyl, branched alkyl, halogen, aryl, aylalkyl, thienylalkyl, furylalkyl, alkoxyl, alkylthio, aryloxy, or arylthio;

$R^4$=H, lower alkyl, branched alkyl, halogen, aryl, arylalkyl, thienylalkyl, furylalkyl, alkoxyl, alkylthio, aryloxy, or arylthio;

T=6π (or 6 pi)-annelated ring system or substituted 6π-annelated ring system (e.g., benzo, pyrido, pyrimido, pyrazino, thieno, furano, pyrrolo, pyrazolo, imidazolo, thiazolo, or oxazolo);

Z=H, lower aLkyl, branched alkyl, aryl, arylalkyl, aryloxy, arylthio, carboxy, alkoxycarbonyl, aryloxycarbonyl arylalkoxycarbonyl, carboxamido, naphthylamino-carbonyl (1- or 2-position), substituted naphthylaminocarbonyl, quinolylamino-carbonyl (2- to 8-position), substituted quinolylaminocarbonyl, naphthylalkylamino-carbonyl (1- or 2-position), quinolylalkylaminocarbonyl (2- to 8-position), thienylaminocarbonyl, substituted thienylaminocarbonyl, furylaminocazbonyl, substituted fiuylaminocarbonyl, or pyridylaminocarbonyl;

W=amino, azaheterocycles, substituted azaheterocycles, hydroxyl, alkoxy, alkylthio, guanidino, or anidino.

Where there are centers of asymmetry, the absolute stereochemistry can be either R or S- configuration and any combination of configurations.

In the generic descriptions of compounds of this invention, the number of atoms of a particular type in a substituent group is generally given as a range. For example, an alkyl group containing from 1 to 4 carbon atoms is indicated as alkyl ($C_1$–$C_4$), or as ($C_{1-4}$) alkyl. Such a range reference is intended to include specific references to groups having each of number of atoms within the specified range. For example, $C_1$–$C_4$ includes each of $C_1$, $C_2$, $C_3$ and $C_4$. Other numbers of atoms and other types of atoms are indicated in a similar manner.

Unless otherwise indicated, the term "alkyl" refers to a branched or unbranched aliphatic hydrocarbon group, preferably having from 1 to 6 carbon atoms, and more preferably 1 to 4 carbon atoms. Preferably the hydrocarbon group is saturated. The alkyl group may optionally be substituted, and some preferred substituents include alkoxy, alkylthio, halogen, amino, monosubstituted amino, disubstituted amino, and carboxy groups.

The term "lower alkyl" refers to an aliphatic hydrocarbon having 1 to 6 carbons, and preferably 1 to 4 carbon atoms (i.e., 1, 2, 3, or 4 carbon atoms). The lower alkyl group may be substituted; preferred substituents include alkoxy, alkylthio, halogen, amino, monosubstituted amino, disubstituted amino, and carboxy.

The term "branched alkyl" refers to a branched aliphatic hydrocarbon. The branched alkyl group is preferably 3 to 10 (i.e., 3, 4, 5, 6, 7, 8, 9 or 10 carbon atoms) carbons, and most preferably 3 to 6 (i.e., 3, 4, 5, or 6 carbon atoms) carbons.

The branched alkyl group may be substituted and some preferred substituents include alkoxy, alkyltlio, halogen, amino, monosubstituted amino, disubstituted amino, and carboxy.

The term "fluoroalkyl" refers to a lower alkyl group which is substituted with a fluorine. The term "perfluoroalkyl" refers to a lower alkyl group which is substituted with a fluorine atom in every available position except for where the lower alkyl group is attached to the main chain.

The term "carboxyalkyl" refers to a chemical moiety with formula —$(R)_n$—COOH, where R is an alkyl moiety, preferably a saturated alkyl, and where n is 0–5.

The term "hydroxyalkyl" refers to a chemical moiety with the formula —$(R)_n$—OH, where R is an alkyl moiety and where n is 1–4.

The term "alkoxy" refers to a chemical substituent of formula —OR, where R is a saturated or unsaturated lower alkyl moiety.

The term "alkylthio" refers to a chemical substituent of formula —SR, where R is a saturated or unsaturated lower alkyl moiety.

The term "aryl" refers to an aromatic group which has at least one ring having a conjugated pi-electron system and includes both carbocyclic aryl (e.g. phenyl) and heterocyclic aryl groups (e.g. pyridine). The aryl group is preferably 6 to 14 carbons, more preferably 6 to 10 carbons. Aryl moieties include monocyclic, bicyclic, and tricyclic rings, where each ring has preferably five or six members. The aryl moiety may be optionally monosubstituted or disubstituted with lower alkyl, hydroxyl, alkoxy, alkylthio, halogen, amino, monosubstituted amino, and disubstituted amino.

The terms "aryloxy" and "arylthio" refer to an aromatic group that is bonded through either oxygen or sulfur, respectively. The aromatic group which has at least one ring having a conjugated pi-electron system and includes both carbocyclic aryl (e.g. phenyl) and heterocyclic aryl groups (e.g. pyridine). The aryl group is preferably 6 to 14 carbons, more preferably 6 to 10 carbons. Aryl moieties include monocyclic, bicyclic, and tricyclic rings, where each ring has preferably five or six members. The aryl moiety may be optionally monosubstituted or disubstituted with lower alkyl, hydroxyl alkoxy, alkylthio, halogen, amino, monosubstituted amino, and disubstituted amino.

The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one non-carbon atom (e.g., N, O, P, S, Se, Si).

Thus, the term "azaheterocycle" refers to a heterocyclic group which includes at least one nitrogen atom in a ring. Preferably the azaheterocyclic group is a N-morpholinyl, N-piperazinyl, N-pyrrolidinyl, N-imidazolyl, N-pyrrolyl, N-pyrazolyl, N-triazolyl, or N-tetrazolyl group. The azaheterocyclic group may also be substituted as recognized in the art, forming a substituted azaheterocycle, preferably a 2-(or 3-) lower alkylmorpholinyl, 2-(3- or 4-) lower alkylpiperazinyl, 2-(or 3-) lower alkylpyrrolidinyl, 2-(or 3-) lower alkylmorpholinyl, 2-(or 3-) lower alkylpyrrolyl group.

The term "monosubstituted aryl" refers to an aryl group substituted with a group selected from alkyl, alkoxy, alkylthio, halogen, hydroxyl, amino, monosubstituted amino, or disubstituted amino.

The term "carbonyl" refers to the group C=O.

The term "cyano" refers to the group —CN.

The term "nitro" refers to the group —$NO_2$.

"Halogen" or "halo" refers to F, Br, Cl, or I, but is preferably F or Cl, and more preferably is F.

"Hydroxyl" or "hydroxy" refers to the group —OH.
"Mercapto" or "thiol" refers to the group —SH.

The term "amino" means the group NRR', where R and R' may independently be alkyl or hydrogen or hydroxyl, but preferably are hydrogen. The term "monosubstituted amino" refers to an amino group in which one of R or R' is alkyl, aryl, arylalkyl, alkoxy, or hydroxy. The term "disubstituted amino" refers to an amino group in which R and R' are each independently alkyl, aryl, arylalkyl, alkoxy, or hydroxy The term "arylalkyl" refers to a lower alkyl group substituted with an aryl group. An example of an arylalkyl group is benzyl where a methyl group is substituted with phenyl. The lower alkyl group may be optionally substituted with a lower alkyl, alkoxy, alkylthio, halogen, amino, mono-substituted amino, or disubstituted ammo. The arylalkyl group may be aryl-substituted where the aryl group is optionally substituted with a lower alkyl, alkoxy, alkylthio, halogen, amino, monosubstituted amino, or disubstituted amino.

The term "thienyl" refers to a group which has the core ring structure of Structure A. The thienyl group may be attached to the rest of the molecule through position 2 or 3 on the ring and may be optionally substituted with lower alkyl, alkoxy, allylthio, halogen, amino, monosubstituted amino, or disubstituted amino.

Structure A

The term "thienylalkyl" refers to a lower alkyl group substituted with a thienyl group. The lower alkyl group may be optionally substituted with a lower alkyl, alkoxy, alkylthio, halogen, amino, monosubstituted amino, or disubstituted amino. The thienylalkyl group may be thienyl-substituted where the thienyl group is optionally substituted with a lower alkyl, alkoxy, alkylthio, halogen, amino, monosubstituted amino, or disubstituted amino.

The term "furyl" refers to a group which has the core ring structure of Structure B. The furyl group may be attached to the rest of the molecule through position 2 or 3 on the ring and may be optionally substituted with lower alkyl, alkoxy, alkylthio, halogen, amino, monosubstituted amino, or disubstituted amino.

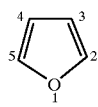

Structure B

The term "furylallyl" refers to a lower alkyl group substituted with a furyl group. The lower alkyl group may be optionally substituted with a lower alkyl, alkoxy, alkylthio, halogen, amino, monosubstituted amino, or disubstituted amino. The furylalkyl group may be furyl-substituted where the furyl group is optionally substituted with a lower alkyl, alkoxy, alkylthio, halogen, amino, monosubstituted amino, or disubstituted amino.

The term "pyridyl" refers to a group which has the core ring structure of Structure C. The pyridyl group may be attached to the rest of the molecule through position 2, 3, or 4 on the ring and may be optionally substituted with lower alkyl, alkoxy, alkylthio, halogen, amino, monosubstituted amino, or disubstituted amino.

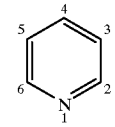

Structure C

The term "pyridylalkyl" refers to a lower alkyl group substituted with a pyridyl group. The lower alllyl group may be optionally substituted with a lower alkyl, alkoxy, alkylthio, halogen, amino, monosubstituted amino, or disubstituted amino. The pyridylalkyl group may be pyridyl-substituted where the pyridyl group is optionally substituted with a lower alkyl, alkoxy, alkylthio, halogen, amino, monosubstituted amino, or disubstituted amino.

The term "6π-annelated ring system" refers to a ring which has 6π electrons and is considered aromatic. The ring may have 6 atoms in its backbone, such a spyridine, pyrimidine, or benzene, or it may have less than 6 atoms in its backbone, such as pyrrole, flran, thiazole, oxazole, or thiophene.

The term "carboxy" refers to the group —COOH.

The term "alkoxycarbonyl" refers to the group ROC(O)—, where R is an alkyl group, as defined herein. If the alkyl group of ROC(O)— is substituted with an aryl group, e.g., benzyl, or phenylethyl, then the group is referred to as an "arylalkoxycarbonyl." The term "aryloxycarbonyl" refers to the group ArOC(O)—, where Ar is an aryl group, as defined herein.

The term "carboxamido" refers to the group —C(O)NH$_2$.

The term "arylamino-carbonyl" refers to the group Ar—NH—C(O)—, where Ar is an aryl group. The Ar group may be naphthyl, quinolyl, thienyl, furyl, or pyridyl, in which case the arylamino-carbonyl group will be called "napthylamino-carbonyl," "quinolylamino-carbonyl," "thienylamino-carbonyl," "furylamino-carbonyl," or "pyridylamino-carbonyl," respectively. The naphthyl group may be attached to the NH moiety at its position 1 or 2 and the quinolyl group may be attached to the NH moiety at its position 2, 3, 4, 5, 6, 7, or 8. All of the above Ar groups may be substituted with common substutuents. If an alkyl group, as defined herein, is interposed between Ar and NH in the above formula, then the group is called an "arylalkylamino-carbonly." Examples include "naphthylalkylamino-carbonyl," "quinolylalkylamino-carbonyl," "thienylalkylamino-carbonyl," "fuylalkylamino-carbonyl," and "pyridylalkylamino-carbonyl."

The term "amino" refers to the group —NH$_2$.

The term "guanidino" refers to the group —HNC(=NH)NH$_2$.

The term "amidino" refers to the group —C(=NH)NH$_2$.

In preferred embodiments, certain efflux pump inhibitors of the present invention have structures that are shown by the generic structure 3 below:

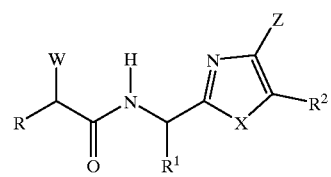

Structure 3 where
X=CH, NR*, O, S (R*=H, lower alkyl, arylalkyl)

R=H, lower alkyl, branched alkyl, fluoroalkyl, carboxyalkyl, hydroxyalkyl, aryl, monosubstituted aryl, disubstituted aryl, 2-(or 3-)thienyl, 2-(or 3-)-furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$ (n=0, 1, 2, 3, or 4); $R^a$ ($R^b$ or $R^c$)=H, lower alkyl, phenyl, benzyl, cyano, hydroxy, or nitro; alternatively $R^a+R^b$ (or $R^b+R^c$)=$(CH_2)_{2-3}$ or —CH=CH—;

$R^1$=H, lower alkyl, branched alkyl, fluoroalkyl, carboxyalkyl, hydroxyalkyl, aryl, 2-(or 3-)thienyl, 2-(or 3-)furyl, or 2-(3- or 4)pyridyl, arylalkyl,thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$ (n=0, 1, 2, 3, or 4); $R^a$ ($R^b$ or $R^c$)=H, lower alkyl, phenyl, benzyl, cyano, hydroxy, or nitro; alternatively $R^a+R^b$ (or $R^b=R^c$)=$(CH_2)_{2-3}$ or —CH=CH—;

$R^2$=H, lower alkyl, branched alkyl;

W=amino, azaheterocycles, substituted azaheterocycles, hydroxy, alkoxy, alkylthio, guanidino, or amidino;

Z=H, lower alkyl, branched alkyl, aryl, amylalkyl, aryloxy, arylthio, carboxy, alkoxycarbonyl, aryloxycarbonyl arylalkoxycarbonyl, carboxamido, naphthylamino-carbonyl (1- or 2-position), substituted naphthylaminocarbonyl, quinolylaminocarbonyl (2- to 8-position), substituted quinolylaminocarbonyl, naphthylalkylaminocarbonyl (1- or 2-position), quinolylalkylaminocarbonyl (2- to 8-position), thienylamino-carbonyl, furylaminocarbonyl, or pyridylaminocarbonyl;

where there are centers of asymmetry, the absolute stereochemistry can be either R or S- configuration and any combination of configuration.

In other preferred embodiments, certain efflux pump inhibitors of the present invention have structures which are shown by the generic structure 4 below:

Structure 4

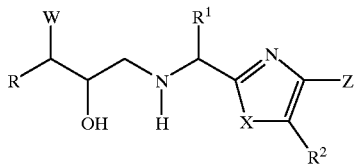

where

X=NR*, O, S (R*=H, lower alkyl, arylalkyl)

R=H, lower alkyl, branched alkyl, fluoroalkyl, carboxyalkyl, hydroxyalkyl, aryl, monosubstituted aryl, disubstituted aryl, 2-(or 3-)thienyl, 2-(or 3-)furyl, 2-(3- or 4-)-pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$ (n=0, 1, 2, 3, or 4); $R^a$ ($R^b$ or $R^c$)=H, lower alkyl phenyl, benzyl, cyano, hydroxy, or nitro; alternatively $R^a=R^b$ (or $R^b+R^c$)=$(CH_2)_{2-3}$ or —CH=CH—;

$R^1$=H, lower aLkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$ (n=0, 1, 2, 3, or 4); $R^a$ ($R^b$ or $R^c$)=H, lower alkyl, phenyl, benzyl, cyano, hydroxy, or nitro; alternatively $R^a+R^b$ (or $R^b+R^c$)=$(CH_2)_{2-3}$ or —CH=CH—;

$R^2$=H, lower alkyl, branched alkyl;

W=amino, azaheterocycles, substituted azaheterocycles, hydroxy, alkoxy, alkyltlio, guanidino, or amidino;

Z=H, lower alkyl, branched alkyl, aryl, arylalkyl, aryloxy, arylthio, carboxy, alkoxycarbonyl, aryloxycarbonyl axylalkoxycarbonyl, carboxamido, naphthylamino-carbonyl (1- or 2-position), quinolylaminocarbonyl (2- to 8-position), naphthylalkylamino-carbonyl (1- or 2-position), quinolylalkylaminocarbonyl (2- to 8-position), thienylaminocarbonyl, furylarninocarbonyl, or pynidylaminocarbonyl; and where there are centers of asymmetry, the absolute stereochemistry can be either R or S- configuration or any combination of configurations.

In yet other preferred embodiments, certain efflux pump inhibitors of the present invention also have structures which are shown by the generic structure 5 below:

Structure 5

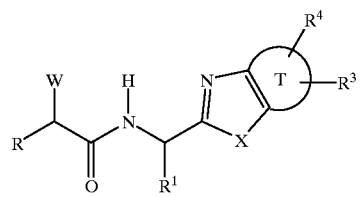

where

X=NR*, O, S (R*=H, lower alkyl, arylalkyl);

R=H, lower alkyl, branched alkyl, fluoroalkyl, carboxyalkyl, hydroxyalkyl, aryl, monosubstituted aryl disubstituted aryl, 2-(or 3-)thienyl, 2-or 3-)furyl, 2-(3- or 4pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$ (n=0, 1, 2, 3, or 4); $R^a$ ($R^b$ or $R^c$)=H, alkyl, phenyl, benzyl, cyano, hydroxy, or nitro; alternatively $R^a+R^b$ (or $R^b+R^c$)= $(CH_2)_{2-3}$ or —CH=CH—;

$R^1$=H, alkyl, branched alkyl, fluoroalkyl, perfluoroalkyl, carboxyalkyl,, aryl,2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$ (n=0, 1, 2, 3, or 4); $R^a$ ($R^b$ or $R^c$)=H, lower alkyl, phenyl, benzyl, cyano, hydroxy, or nitro; alternatively $R^a+R^b$ (or $R^b+R^c$)=$(CH_2)_{2-3}$ or —CH=CH—;

$R^3$=H, lower alkyl, branched alkyl, halogen, aryl, arylalkyl, thienylalkyl, furylalkyl, alkoxyl, alkylthio, aryloxy, or arylthio;

$R^4$=H, lower alkyl, branched alkyl, halogen, aryl, arylalkyl, thienylalkyl, furylalkyl, alkoxyl, alkylthio, aryloxy, or arylthio;

T=6π(or 6 pi)-annelated ring system or substituted 6π-annelated ring system (e.g., benzo, pyrido, pynimido, pyrazino, thieno, furano, pyrrolo, pyrazolo, imidazolo, thiazolo, or oxazolo);

W=amino, azaheterocycles, substituted azaheterocycles, hydroxy, alkoxy, alkylthio, guanidino, or amidino; and where there are centers of asymmetry, the absolute stereochemistry can be either R or S- configuration and any combination of configuration.

In preferred embodiments, certain efflux pump inhibitors of the present invention also have structures which are shown by the generic structure 6 below:

Structure 6

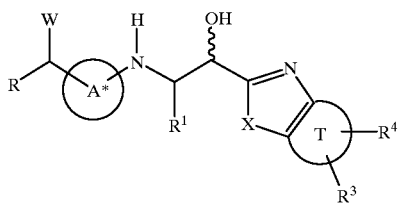

where
A*=CH(OH)CH$_2$, C=O;
R=H, lower alkyl, branched alkyl, fluoroalkyl, carboxyalkyl, hydroxyalkyl, aryl, monosubstituted aryl, disubstituted aryl, 2-(or 3-)thienyl, 2-(or 3-)fwyl, 2-(3- or 4-pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, (CH$_2$)$_n$N=CNR$^b$R$^c$ (n=0, 1, 2, 3, or 4); R$^a$ (R$^b$ or R$^c$)=H, alkyl, phenyl, benzyl, cyano, hydroxy, or nitro; alternatively R$^a$+R$^b$ (or R$^b$+R$^c$)=(CH$_2$)$_{2-3}$ or —CH=CH—;

R$^1$=H, alkyl, branched alkyl, fluoroalkyl, perfluoroalkyl, carboxyaLkyl,, aryl,2-(or 3-)thienyl, 2-(or 3-)furyl, or 2-(3- or 4)pyridyl, arylalkyl, thienylalkyl, furylalkyl, pyridylalkyl, (Ch$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, (CH$_2$)$_n$N=CNR$^b$R$^c$ (n=0, 1, 2, 3, or 4); R$^a$ (R$^b$ or R$^c$)=H, lower alkyl, phenyl, benzyl, cyano, hydroxy, or nitro; alternatively R$^a$+R$^b$ (or R$^b$+R$^c$)=(CH$_2$)$_{2-3}$ or —CH=CH—;

R$^3$=H, lower alkyl, branched alkyl, halogen, aryl, arylalkyl, thienylalkyl, furylalkyl, alkoxyl, alkylthio, aryloxy, or arylthio;

R$^4$=H, lower alkyl, branched alkyl, halogen, aryl, arylalkyl, thienylalkyl, furylalkyl, alkoxyl, alkylthio, aryloxy, or arylthio;

T=6π (or 6 pi)-annelated ring system or substituted 6π-annelated ring system (e.g., benzo, pyrido, pyrimido, pyrazino, thieno, flimno, pyrrolo, pyrazolo, imidazolo, thiazolo, or oxazolo);

W=amino, azaheterocycles, substituted azaheterocycles, hydroxy, alkoxy, alkylthio, guanidino, or amidino; and where there are centers of asymmetry, the absolute stereochemistry can be either R or S- configuration and any combination of configuration.

The generic compound descriptions above should be understood to include additional narrower generic descriptions in which the possible substituents for one or more of the specified substituent groups or substitutions (e.g., W, R, R$^1$, R$^2$, R$^3$, R$^4$, A*, Z*) is limited to a subset of the listed groups.

Compounds within the generic description above can be obtained by synthetic chemistry methods known to those slilled in the chemical arts as described in the Examples below. Specific examples of compounds within the generic description are provided in the Detailed Description below in connection with Table 1.

Reference to efflux pump inhibitors in the aspects of the invention described below refers to compounds within the generic compound descriptions above, set forth in Structures 1–6, with all the descriptions and limitations set forth herein, having efflux pump inhibitor activity.

A particularly appropriate example of a microbe appropriate for the use of an efflux pump inhibitor is a pathogenic bacterial species, *Pseudomonas aeruginosa*, which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is adnministered in conjunction with the efflux pump inhibitor, the antibacterial agent, which would otherwise be maintained at a very low intracellular concentration by the export process, can accumulate to a concentration which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

In addition as suggested above, for some microbial, e.g., bacterial, species, efflux pump inhibitors can decrease the virulence of the microbe, for example, by inhibiting the transport of factors important for pathogenicity. Again using *P. aeruginosa* as an example, inhibition of an efflux pump in this bacterium inhibits the uptake of iron, which is inportant for pathogenicity. The mechanism of bacterial iron transport involves molecules called siderophores, which are synthesized and exported by bacterial cells via efflux pumps. These siderophores bind tightly to iron scavenged from the host, and are then taken up by the bacteria. In this way, the iron needed for bacterial metabolism is obtained, and an infection can be maintained.

Therefore, illustrating the utility of efflux pump inhibitors, inhibiting the efflux pump of *P. aeruginosa* allows obtaining one or more of the following biological effects:

1. *P. aeruginosa* strains will become susceptible to antibiotics that could not be used for treatment of pseudomonad infections, or become more susceptible to antibiotics which do inhibit pseudomonal growth.

2. *P. aeruginosa* sins will become more susceptible to antibiotics currently used for treatment of pseudomonad infections.

3. Virulence of *P. aeruginosa* will be attenuated because the availability of iron will be hampered 4. The inhibition of the pump or of one of the components of the pump may be lethal or prevent growth.

Obtaining even one of these effects provides a potential therapeutic treatment for infections by this bacterium. Also, as previously mentioned, similar pumps are found in other microorganisms. Some or all of the above effects can also be obtained with those microbes, and they are therefore also appropriate targets for detecting or using efflux pump inhibitors. Thus, the term "microbes" include, for example, bacteria, fungi, yeasts, and protozoa As indicated, the bacterium to be inhibited through the use of an efflux pump inhibitor can be from other bacterial groups or species, such as one of the following: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella* bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hicus subsp. hyicus, Staphylococcus haemolyticus, Staphylococcus hominis, Staphylococcus saccharolyticus.

The term "efflux pump" refers to a protein assembly which exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump which spans the outer membrane. Certain efflux pumps will include a polypeptide which has at least 50% amino acid sequence similarity with a polypeptide which is part of the *Pseudomonas aeruginosa* mexA/mexB/oprM efflux pump or the efflux pump overexpressed by *P. aeruginosa* Strain K385, or the efflux pump overexpressed by *P. aeruginosa* Strain PAO4098E. Due to the described sequence similarity of a component polypeptide of the efflux pump, such an efflux pump is termed a *Pseudomonas aeruginosa*-type efflux pump.

The term "non-tetracycline-specific efflux pump" refers to an efflux pump which is not highly specific for tetracycline (relative to other antibiotics) and thus is not a tetracycline (tetracycline-specific) efflux pump. The term thus includes broad substrate pumps (efflux a number of compounds with varying structural characteristics) and pumps which are highly specific for compounds (including antibiotics) other than tetracyclines. Tetracycline efflux pumps are involved in specific resistance to tetracycline in bacteria (Speer et al., 1992, *Clin. Microbiol. Rev.* 5: 387–399.) As noted, these pumps are highly specific for tetracyclines, and their presence confers high tetracycline resistance to the cell. However, they do not confer resistance to other antibiotics. The genes for the tetracycline pump components are found in plasmids in Gram-negative as well as in Gram-positive bacteria and can be divided in two main groups, tetA(A-E), and tetK and tetL. TetA-E tetracycline resistance determinants contain a structural gene, tetA, which is a tetracycline specific pump, and a repressor gene, tetR, that mediates inducible resistance to tetracyclines. Tetracycline efflux pumps belonging to this group are designated tetA(A), tetA(B), tetA(D), and tetA(E), and are found in Enterobacteriaceae and other Gram-negative bacteria TetK and TetL are pumps involved in tetracycline resistance in Gram-positive bacteria. The genes are regulated via translational attenuation and are not homologous to tetA group.

An "efflux pump inhibitor" is a compound which specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity. Of particular interest in this invention, are compounds which inhibit the export or activity of efflux pumps which have a broad substrate range which includes antibacterial agents. The term "non-tetracycline-specific efflux pump inhibitor" refers to an efflux pump inhibitor which inhibits a non-tetracycline-specific efflux pump. The term "*Pseudomonas aeruginosa*-type efflux pump inhibitor" refers to an efflux pump inhibitor which inhibits a *Pseudomonas aenuginosa*-type efflux pump. A "*Pseudomonas aeruginosa* efflux pump inhibitor" is an efflux pump inhibitor which inhibits the export activity of an efflux pump found in *Pseudomonas aeruginosa*.

By "comprising" it is meant including, but not limited to, whatever follows the word "comprising." Thus, use of the term "comprising" indicates that the listed elements are required or mandatory, but that other elements are optional and may or may not be present. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In another aspect, this invention provides a method for treating a microbial infection, e.g., a bacterial infection, in an animal by administering to an animal suffering from such an infection an efflux pump inhibitor as described above in an amount sufficient to reduce efflux pump activity.

In a preferred embodiment, the inhibitor is one which decreases the pathogenicity of the microbe. Such a decrease in pathogenicity can be obtained, for example, by interfering with bacterial iron acquisition by inhibiting the transport of siderophores. The pathogenicity may also be reduced by reducing or eliminating the microbial products which cause tissue-damaging effects to the host. Other methods of reducing pathogenicity are, however, also within this aspect. The animal may be, for example, chickens and turkeys, and in certain preferred embodiments is a mammal, e.g., a human.

In certain preferred embodiments, the microbial infection may be due to bacteria, which may, for example, be any of the bacterial species indicated above, but specifically including *Pseudomonas aeruginosa*.

In a related aspect, this invention provides a method of treating an animal suffering from a microbial infection by administering to the animal an efflux pump inhibitor in an amount sufficient to reduce efflux pump activity. In this aspect, the efflux pump inhibitor is one which reduces the in vivo viability of a microbe involved in the infection. By reducing the in wvo viability, the infected animal can more readily clear its body of the infection, or the microbes may even be killed. In particular embodiments the animal is a mammal Also in particular embodiments, the microbe may be from one of a variety of pathogenic bacterial species, specifically including those listed above.

The term "in vivo viability" refers to the ability of a microbe, e.g., a bacterium, to survive or grow in a host, such as an animal. Therefore, an efflux pump inhibitor which reduces the in vivo viability of a microbe may stop the growth of the microbe and/or kill the microbe. Such efflux pump inhibitors, therefore are antimicrobial agents.

In a further related aspect, this invention includes a method for prophylactic treatment of an animal, e.g., a mammal. In this method, an efflux pump inhibitor which reduces the pathogenicity of a microbe is administered to a mammal at risk of a microbial infection, e.g., a bacterial infection.

In a related aspect, the invention provides a method for treating a microbial infection in an animal, specifically including in a mammal, by treating an animal suffering from such an infection with an antimicrobial agent and an efflux pump inhibitor. The combination of an antimicrobial agent and an efflux pump inhibitor may increase the susceptibility of the microbe for that antimicrobial agent. In this way a microbe involved in the infection can be treated using the antimicrobial agent in smaller quantities, or can be treated with an antimicrobial agent which is not therapeutically effective when used in the absence of the efflux pump inhibitor. Thus, this method of treatment is especially appropriate for the treatment of infections involving microbial strains which are difficult to treat using an antimicrobial agent alone due to a need for high dosage levels (which can cause undesirable side effects), or due to lack of any clinically effective antimicrobial agents. However, it is also appropriate for treating infections involving microbes which are susceptible to particular antimicrobial agents as a way to reduce the dosage of those particular agents. This can reduce the risk of side effects, but can also reduce the selection effect for highly resistant microbes resulting from the consistent high level use of a particular antimicrobial agent. In particular embodiments the microbe is a bacterium, which may, for example, be from any of the groups or species indicated above. Also in particular embodiments various antibacterial agents can be used. These include quinolones, tetracyclines, glycopeptides, aminoglycosides, beta-lactams, rifamycins, macrolides, oxazolidinones, coumermycins, and chloramphenicol. In particular embodiments an antibiotic of the above classes can be, for example, one of the following:

β-Lactam Antibiotics imipenem, meropenem, biapenem, cefaclor, cefadroxil, cefamandole, cefatrizine, cefazedone, cefazolin, cefixime, cefinenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763

Macrolides azitliromycin, clarithiromycin, erythromycin, oleandomycin, rokitamycin, rosaramicin, roxitliromycin, troleandomycin Quinolones amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, PD131628, PD138312, PD140248, Q-35, AM-1155, NM394, T-3761, rufloxacin, OPC-17116, DU-6859a (Sato, K. et al., 1992, *Antimicrob Agents Chemother.* 37:1491–98), DV-7751a (Tanaka, M. et al., 1992, *Antimicrob. Agents Chemother.* 37:2212–18)

Tetracyclines and Oxazolidinones chlortetracycline, demeclocycline, doxycycline, lymecycline, methacycline, minocycline, oxytetracycline, tetracycline, linezolide, eperozolid Aminoglycosides amikacin, arbekacin, butirosin, dibekacin, fortimicins, gentamicin, kanamycin, meomycin, netilmicin, ribostamycin, sisomicin, spectinomycin, streptomycin, tobramycin, clindamycin, lincomycin Oxazolidinones Linezolid(U-100766), eperezolide(U-100592).

Each of the above compounds have been reported in the literature. Other antibiotic compounds which may be identified which are effluxed by particular bacteria can also be utilized with the efflux pump inhibitors of this invention.

In a further related aspect, this invention includes a method for prophylactic treatment of a mammal. In this method, an antimicrobial agent and an efflux pump inhibitor is administered to a mammal at risk of a microbial infection, e.g. a bacterial infection.

In the context of the response of a microbe, such as a bacterium, to an anti-microbial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (AEC) of that antimicrobial agent will have been reduced.

As used herein, the term "treating" refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a potentiator and an antibacterial (or antimicrobial) agent in combination (either simultaneously or serially).

By "therapeutically effective amount" or "pharmaceutically effective amount" is meant an amount of an efflux pump inhlbitor, or amounts individually of an eflux pump inhibitor and an antimicrobial agent, as disclosed for this invention, which have a therapeutic effect, which generally refers to the inhibition to some extent of the normal metabolism of microbial cells causing or contributing to a microbial infection. The doses of efflux pump inhibitor and antimicrobial agent which are useful in combination as a treatment are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determiined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective if a microbial infection existed.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

The term "microbial infection" refers to the invasion of the host mammal by pathogenic microbes. This includes the excessive growth of microbes which are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection.

The term "administration" or "administering" refers to a method of giving a dosage of an antimicrobial pharmaceutical composition to a mammal, where the method is, e.g., topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

The term "mammal" is used in its usual biological sense. Thus, it specifically includes humans, cattle, horses, dogs, and cats, but also includes many other species.

In another aspect, this invention also features a method of inhibiting a membrane channel in a cellular membrane, involving contacting the membrane channel with a membrane channel inhibitor, where the inhibitor reduces the effluxing capacity of the membrane channel. In specific embodiments, at least one polypeptide of the membrane channel has at least 50% amino acid sequence similarity with a polypeptide of the mexA/mexB/oprM efflux pump, or of the efflux pump overexpressed by *Pseudomonas aeruginosa* Stain K385.

As used herein, the term "membrane channel" refers to a protein assembly located in the cellular membrane of a cell which allows the transport of one or more types of molecules across the membrane. Such transport may be either passive transport in response to concentration gradients, or may be active transport which depends upon a cellular energy source.

A "membrane chanmel inhibitor" then is, similar to an efflux pump inhibitor, a compound which slows or prevents the transport of molecules across the cellular membrane using the corresponding membrane channel.

This invention also features a method of enhancing the antimicrobial activity of an antimicrobial agent against a microbe, in which such a microbe is contacted with an efflux pump inhibitor, e.g., a non-tetracycline specific efflux pump inhibitor, to an efflux pump in the cell, and an antibacterial agent. The efflux pump inhibitor is a compound as described above. Thus, this method makes an antimicrobial agent more effective against a cell which expresses an efflux pump when the cell is treated with the combination of an antimicrobial agent and a non-tetracycline-specific efflux pump inhibitor. In particular embodiments the microbe is a bacterium or a fungus, such as any of those indicated in the first aspect above; the antibacterial agent can be selected from a number of structural classes of antibiotics including, e.g., beta-lactams, glycopeptides, aminoglycosides, quinolones, oxazolidinones, tetracyclines, rifamycins, coumermycins, macrolides, and chloramphenicol. In particular embodiments an antibiotic of the above classes can be as stated above.

In a further aspect this invention provides pharmaceutical compositions effective for treatment of an infection of an animal, e.g., a mamnmal, by a microbe, such as a bacterium or a fungus. The composition includes a pharmaceutically acceptable carrier and an efflux pump inhibitor as described above. In preferred embodiments, such compositions contain efflux pump inhibitors which are themselves effective antimicrobial agents, even in the absence of another antimicrobial agent (i.e., have intnnsic antimicrobial activity). Thus, pharmaceutical compositions including such efflux pump inhibitors can be used either alone or in conjunction with another antimicrobial agent. Also in preferred embodiments, the efflux pump inhibitors in pharmaceutical compositions of this aspect are efflux pump inhibitors which enhance the effectiveness of an annmmcrobial agent other than the efflux pump inhibitor, so such compositions would generally be used in combination with such other antimicrobial agent. The invention also provides pharmaceutical compositions similarly effective for treatment of an infection of a mammal which include an efflux pump inhibitor and an antimicrobial agent. Similarly, the invention provides antimicrobial formulations which include an antimicrobial agent, an efflux pump inhibitor, and a carrier. In preferred embodiments, the antimicrobial agent is an antibacterial agent.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the *Merck Index,* Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics.* 8th Ed., Pergamon Press.

In yet another aspect, the invention provides a method of suppressing growth of a microbe, e.g., a bacterium, expressing an efflux pump, e.g., a non-tetracycline-specific efflux pump. As illustrated by the case where the microbe is a bacterium, the method involves contacting that bacterium with an efflux pump inhibitor, e.g., a non-tetracycline-specific efflux pump inhibitor, in the presence of a concentration of antibacterial agent below the MIC of the bacterium. This method is useful, for example, to prevent or cure contamination of a cell culture by a bacterium possessing an efflux pump. However, it applies to any situation where such growth suppression is desirable.

In a related aspect, the invention provides a method of suppressing growth of a microbe, e.g., a bacterium, which involves contacting the microbe with an efflux pump inhibitor which reduces the expression of a component of an efflux pump. Such an inhibitor can act on the regulation of that expression in number of different ways. It may, for example, enhance the production of a repressor molecule which prevents expression of an efflux pump component. Another possible mechanism is if the inhibitor blocks the release of a repressor molecule. Examples of such a repressor is MarR in *E. coli* (Seoane and Levy, 1994, *Abstr. of the Am. Soc. for Microbiol. Gen. Meeting,* Las Vegas, Nev., Abstr. H-26). An example of a positive regulator is BmrR in *Bacillus subtilis* (Ahmed et al., 1994, *J Biol. Chem.*).

In another related aspect, the invention provides a method for reducing a population of a microbial, e.g., a bacterial strain, involving contacting the population with an efflux pump inhibitor which inhibits a component of an efflux pump expressed in the microbe in that population, which is essential for the growth of the microbe expressing that efflux pump. In particular embodiments, that component is a cytoplasmic membrane component. As indicated above, such efflux pump inhibitors may act in various ways, including, but not limited to, acting directly on the essential component, or acting to inhibit the expression of that component.

The term "reducing a population" means that the microbes of that population are being killed. This is distinguished from the action of a static agent, e.g. a bacteriostatic agent, which prevents the bacteria from growing and multiplying but does not kill the microbes. Accordingly, in the context of this aspect, an "essential component" of an efflux pump is one which is essential to the in vivo survival of the microbe, i.e., the survival in a host.

In yet another aspect, this invention provides a method for enhancing growth of an animal by administering an efflux pump inhibitor to the animal, which inhibits an efflux pump expressed in a bacterial strain in the animal, and which inhibits the growth of that bacterial strain. Such a growth enhancing effect may result from the reduced energy consumption by the bacteria, which increases the food energy available to the animal. This method is appropriate, for example, for use with cattle, swine, and fowl such as chickens and turkeys.

In an additional aspect, the invention provides novel compounds having efflux pump activity. These compounds have chemical structures as described above.

In a further aspect, the invention provides a method of making a pharmaceutical composition comprising the steps of identifying an efflux pump inhibitor having a chemical structure as set forth in Structure 1 or Structure 2 or the sub-generic structures 3, 4, 5 and 6, as described herein; synthesizing said efflux pump inhibitor in an amount sufficient to provide a therapeutic response; and preparing a pharmaceutical composition containing said efflux pump inhibitor. The efflux pump inhibitor may have the chemical structure as described above. The pharmaceutical composition may also contain one or more antimicrobial agents, e.g., as identified above, and one or more carriers, diluents, and excipients. Further, in preferred embodiments, the efflux inhibitor compound is active against a microbe, e.g., a bacteriamn, as identified above.

As indicated above, while the present invention is presently exemplified by activity against bacteria, compounds of the present invention also have activity against other microbes, for example against yeasts and/or other fungi. Thus, the above aspects also include embodiments in which described compounds are active or effective against such other microbes.

Other features and advantages of the invention will be apparent from the following description of the preferred embodiments, and from the claims.

DESCRIPTION OF THE PREFERRED EMBODIMENTS

Identification of Efflux Pump Inhibitors

Initial identification of efflux pump inhibitors having structures as described for the present invention was performed using a screening method as generally described in Trias et al., EFFLUX PUMP INHIBITORS, U.S. application. No. 08/427,088, Trias et al., EFFLUX PUMP IBITORS, U.S. Appl. No. not yet assigned, filed Jul. 22, 1997; Trias et al., International Application No. PCT/US96/05469, International Publication No. WO 96/33285, entitled EFFLUX PUMP INHIBITORS. In particular, the screening method based on inhibition of microbial growth in the presence of a subinhibitory concentration of an antibacterial agent which is normally effluxed by the test microbe and a concentration of a test compound was used for indentifying some of the active compounds disclosed herein. In this method, inhibition of growth of the microbe is indicative that export of the antibacterial agent is inhibited by the test compound, and that the test compound is therefore an efflux pump inhibitor. The mode of action of the test compound so identified can then be comfirmed as inhibiting active efflux. However, other screening methods for detecting efflux pump inhibitors can also be used, specifically including the additional methods described in the above references.

Synthesis of Derivatives of Efflux Pum Inhibitors from Screening

Exemplary compounds of the present invention were synthesized by methods as described in the Examples below. Those skilled in the art will understand how to synthesize additional compounds within the scope of this invention based on the described syntheses and the knowledge of those skilled in the art of chemical synthesis.

Susceptibility Testing

Particular exemplary efflux pump inhibitor compounds within the generic descriptions of the compounds of this invention were evaluated for potentiation effect. The in vitro microbiological data for antibiotic potentiation is presented in Table 1 below.

Potentiation effect is observed by the reduction of the minimum inhibitory concentration of levofloxacin in the presence of the experimental efflux pump inhibitor. The activity of efflux pump inhibitors (EPI) in combination with fluoroquinolones, such as levofloxacin, is assessed by the checkerboard assay (Antimicrobial Combinations. In Antibiotics in Laboratory Medicine, Ed. Victor Lorian, M.D., Fourth edition, 1996, pp 333–338) using broth microdilution method performed as recommended by the NCCLS (National Committee for Clinical Laboratory Standards (NCCLS). 1997. Methods for Dilution of Antimicrobial Susceptibility Tests for Bacteria That Grow Aerobically—Fourth Edition; Approved Standard. NCCLS Document M7-A4, Vol 17 No.2). The test organism used is *Pseudomonas aeruginosa* PAM1001. The compounds of this invention demonstrate pump inhibitory activity against a broad-range of *P. aeruginosa* over-producing singular efflux pumps (MexAB, MexCD, and MexEF) and clinical strains containing multiple efflux pumps, not limited to the Mex classification. The compounds tabulated below are representative of the described invention.

In this assay, multiple dilutions of two drugs, namely the EPI and levofloxacin, are being tested, alone and in combination, at concentrations equal to, above and below their respective minimal inhibitory concentrations (MICs). In the case of EPI, most of these compounds are devoid of intrinsic antimicrobial activity and are tested at the maximum concentration of 40 μg/mL. The MIC of levofloxacin against *P. aeruginosa* PAM1001 is 4 μg/mL.

The EPI tested are readily soluble in water and stock solutions are prepared at a final concentration of 2 mg/mL. Stock solutions are further diluted, according to the needs of a particular assay, in Mueller Hinton Broth (MHB). Stock solution can be stored at −80° C. Quinolones are solubilized according to the instructions of the manufacturers, at a concentration of 1 mg/mL. They are then firrther diluted in MSB. Stock solution can be stored at −80° C.

The checkerboard assay is performed in microtiter plates. Levofloxacin is diluted in the x axis, each column containing a single concentration of levofloxacin. The EPI is diluted in the y axis, each row containing an equal concentration of EPI. The result of these manipulations is that each well of the microtiter plate contains a unique combination of concentrations of the two agents. Each EPI are tested independently.

The assay is performed in MHB with a final bacterial inoculum of $5 \times 10^5$ CFU/mL (from an early-log phase culture). Microtiter plates are incubated during 20 h at 35° C. and are read using a microtiterplate reader (Molecular Devices) at 650 nm as well as visual observation using a microtiter plate reading mirror. The MIC is defined as the lowest concentration of quinolone, within the combination, at which the visible growth of the organism is completely inhibited.

| Efflux Pump Inhibitors (EPIs) for Table 1 | |
|---|---|
| Comp | Structure |
| 1 | Ethyl 2-[(IR)-1-[(2R)-2,5-diaminovaleramido]-3-phenylpropyl]-4-oxazole-carboxylate Trifluoroacetate |
| 2 | Benzyl 2-[(1R)-1-[(2R)-2,5-diaminovaleramido]-3-phenylpropyl]-4-oxazole-carboxylate Trifluoroacetate |
| 3 | Benzyl 2-[(1R)-1-[(2R)-2,5-diaminovaleramido]-3-(2-naphthyl)propyl]-4-oxazolecarboxamide Trifluoroacetate |
| 4 | 2-[(1R)-1-[(2R)-2,5-Diaminovaleramido]-3-phenylpropyl]-N-(2-naphthyl)-4-oxazolecarboxamide Trifluoroacetate |
| 5 | 2-[(1R)-1-[(2R)-2,5-Diaminovaleramido]-3-phenylpropyl]-N-(3-quinolyl)-4-oxazolecarboxamide Trifluoroacetate |
| 31 | (2R)-2,5-Diamino-N-[(1R)-1-[(RS)-(2-benzoxazolyl)hydroxymethyl]-3-phenyl-propyl]valeramide Trifluoroacetate |
| 32 | (2R)-2,5-Diamino-N-[(1R)-1-[(RS)-(5-tert-butyl-2-benzoxazolyl)hydroxymethyl]-3-phenylpropyl]-valeramide Trifluoroacetate |
| 33 | (2R)-2,5-Diamino-N-[(1R)-1-[(RS)-(5,6-dimethyl-2-benzoxazolyl)hydroxymethyl]-3-phenylpropyl]-valeramide Trifluoroacetate |
| 34 | (2R)-2,5-Diamino-N-[(1R)-1-[(RS)-(5-chloro-2-benzoxazolyl)hydroxymethyl]-3-phenylpropyl]valeramide Trifluoroacetate |
| 35 | (2R)-2,5-Diamino-N-[(1R)-1-[(RS)-(2-benzimidazolyl)hydroxymethyl]-3-phenylpropyl]valeramide Trifluoroacetate |
| 36 | (2R)-2,5-Diamino-N-[(1R)-1-[(RS)-(1-oxazolo[4,5-b]pyridin-2-yl)hydroxymethyl]-3-phenylpropyl]-valeramide Trifluoroacetate |
| 37 | (2R)-2,5-Diamino-N-[(IR)-1-[(RS)-(2-benzothiazolyl)hydroxymethyl]-3-phenylpropyl]valeramide Trifluoroacetate |
| 61 | 2-[(1R)-1-[[(2RS, 3R)-3,6-Diamino-2-hydroxyhexyl]amino)-3-phenylpropyl]-N-(3-quinolyl)-4-oxazolecarboxamide Trifluoroacetate |
| 62 | (2RS, 3R)-3,6-Diamino-1-[[(1R)-1-[(RS)-(5,6-dimethyl-2-benzoxazolyl)-hydroxymethyl]-3-phenylpropyl]amino]-2-hexanol Trifluoroacetate |

TABLE 1

Levofloxacin MIC Against *P. aeruginosa* PAM1001 in Presence of Efflux Pump Inhibitor (EPI)

| | Minimum Inhibitory Concentration (µg/mL) | | | | | | | |
|---|---|---|---|---|---|---|---|---|
| Compound | EPI Conc. 0 µg/mL | EPI Conc. 0.625 µg/mL | EPI Conc. 1.25 µg/mL | EPI Conc. 2.5 µg/mL | EPI Conc. 5 µg/mL | EPI Conc. 10 µg/mL | EPI Conc. 20 µg/mL | EPI Conc. 40 µg/mL |
| 1 | 4 | 4 | 4 | 4 | 4 | 4 | 2 | 1 |
| 2 | 4 | 4 | 4 | 4 | 2 | 0.125 | 0.015 | 0.125 |
| 3 | 4 | 4 | 4 | 2 | 0.015 | 0.015 | 0.015 | 0.008 |
| 4 | 4 | 4 | 4 | 4 | 4 | 4 | 4 | 4 |
| 5 | 4 | 4 | 4 | 0.5 | 0.008 | 0.008 | 0.015 | 0.015 |
| 31 | 4 | 4 | 4 | 2 | 1 | 0.5 | 0.125 | 0.06 |
| 32 | 4 | 4 | 0.5 | 0.015 | 0.03 | 0.03 | 0.03 | 0.03 |
| 33 | 4 | 4 | 2 | 0.06 | 0.03 | 0.015 | 0.015 | 0.015 |
| 34 | 4 | 4 | 2 | 2 | 0.03 | 0.015 | 0.015 | 0.015 |
| 35 | 4 | 4 | 4 | 4 | 2 | 1 | 0.25 | 0.125 |
| 36 | 4 | 4 | 4 | 4 | 4 | 4 | 2 | 2 |
| 37 | 4 | 4 | 4 | 4 | 1 | 1 | 0.125 | 0.06 |
| 61 | 4 | 4 | 2 | 2 | 0.06 | 0.03 | 0.03 | 0.015 |
| 62 | 4 | 2 | 0.5 | 0.06 | 0.03 | 0.03 | 0.03 | 0.03 |

In vivo Evaluation of Efflux Pump Inhibitor Compounds

Inhibitors of the bacterial efflux pumps are generally initially characterized in vitro. Those which show effective inlhibition of the pump(s) and which show synergistic activity with antibiotics are selected for evaluation in vivo. Efficacy testing will be done using standard procedures. Primary efficacy evaluation may be done using the murine septicemia model (M. G. Bergeron, 1978, *Scand. J Infect. Dis.* Suppl. 14:189–206; S. D. Davis, 1975, *Antimicrob. Agents Chemother.* 8:50–53). In this model a supra-lethal dose of bacteria is used to challenge the rodents. Treatment is initiated, varying either or both time(s) of treatment and dose of antibiotic. In these experiments both the antibiotic and the efflux pump inhibitor doses are varied. A positive result is indicated by significant increase in protection from the lethal infection by the combination of the potentiator (the efflux pump inhibitor) and the antibiotic versus the antibiotic alone.

A second efficacy model which is used is the mouse soft tissue infection model (Vogelman et al., 1988, *J Infect. Dis.* 157:287–298). In this model anesthetized mice are infected with an appropriate titer of bacteria in the muscle of the hind thigh. Mice are either neutropenic (cyclophosphamide treated at 125 mg/kg on days -4, -2, and 0) or immunocompetent. The infecting dose is commonly $10^5$–$10^6$ colony forming units per animal. Treatment with the combination of the efflux pump inhibitor and/or antibiotics follows infection, or can occur before infection. The proliferation (or death) of the bacteria within the thigh muscle is monitored over time. Effective combinations show greater activity than the antibiotic alone. Activity is defined as reduction in growth rate of the test bacteria in the murine tissue.

Another model useful for assessing the effectiveness of the efflux pump inhibitors is the diffusion chamber model (Malouin et al., 1990, *Infect. Immun.* 58:1247–1253; Day et al., *J. Infect.* 2:39–51; Kelly et al., 1989, *Infect. Immun.* 57:344–350). In this model rodents have a diffusion chamber surgically placed in their peritoneal cavity. The chamber can consist of a polypropylene cylinder with semipermeable membranes covering the cylinder ends. Diffusion of peritoneal fluid into and out of the chamber provides nutrients for the microbes. The proliferation of the bacteria in the presence and absence of the antibiotic/efflux pump inhibitor is compared to the antibiotic alone. Dose ranging of the combination and the antibiotic alone are done to assess effectiveness of the antimicrobial and combinations. A tertiary model useful as a stringent test of the efflux pump inhibitor/antibiotic combination is the endocarditis model (J. Santoro and M. E. Levinson, 1978, *Infect. Immun.* 19:915–918). Either rats or rabbits are effectively used in this model. The effectiveness of combinations of efflux inhibitor and antibiotic are compared to antibiotic alone. The end point is usually viable cells remaining in the cardiac vegetations at the end of treatment.

The examples of infection models provided are not limifing. As understood by those skilled in the art, other models can be utilized as appropriate for a specific infecting microbe. In particular, cell-based infection models may be used in some circumstances instead of animal models.

Pharmaceutical Compositions and Modes of Administration

The particular compound that is an efflux pump inhibitor can be administered to a patient either by itself, or in combination with an antimicrobial, e.g., antibacterial, agent, or in pharmaceutical compositions where it is mixed with suitable carriers or excipient(s). A combination of an efflux pump inhibitor with an antimicrobial agent can be of at least two different types. In one, a quantity of an efflux pump inhibitor is combined with a quantity of an antimicrobial agent in a mixture, e.g., in a solution or powder mixture. In such mixtures, the relative quantities of the inhibitor and the antimicrobial agent may be varied as appropriate for the specific combination and expected treatment. In a second type of combination an inhibitor and an antimicrobial agent can be covalently linked in such manner that the linked molecule can be cleaved within the cell. However, the term "in combination" can also refer to other possibilities, including serial administration of an inhibitor and another antimicrobial agent. In addition, an efflux pump inhibitor and/or another antimicrobial agent may be administered in pro-ig forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. It is preferable that the therapeutic serum concentration of an efflux pump inhibitor should be in the range of 0.1–100 µg/mL, more preferably 0.1–50 µg/mL, 0.1–20 µg/mL, 1.0–50 µg/mL, or 1.0–20 µg/mL.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

In particular preferred embodiments, the efflux inhibitor in a pharmaceutical composition has a structure as shown by the generic structures described above. The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treaanent to higher levels if the clinical response were not adequate (precluding toxicity). The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific infection being treated, such agents may be formulated and administered systemically or locally. Techniques for formulation and administration may be found in *Reminton's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art, into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrobdone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffn, or liquid polyethylene glycols. In addition, stabilizers may be added.

EXAMPLES

The examples below are non-limiting and are merely representative of various aspects and features of the present invention. The examples describe the method of synthesis of the compounds of the invention.

Example 1
Synthesis of the Compounds of the Invention

The compounds of the present invention may be readily prepared in accordance with the following synthesis schemes, as illustrated in the specific procedures provided. However, those skilled in the art will recognize that other synthetic pathways for forming the compounds of this invention can be utilized, and that the following is provided merely by way of example, and is not limiting to the present invention. It will be farther recognized that various protecting and deprotecting strategies will be employed which are standard in the art (see, e.g., "Protective Groups in Organic Synthesis" by Greene and Wuts). Those skilled in the arts will recognize that the selection of any particular protecting group (e.g., amine and carboxyl protecting groups) will depend on the stability of the protected moiety with regards to the subsequent reaction conditions and will understand the appropriate selections.

Further illustrating the knowledge of those skilled in the art is the following sampling of the extensive chemical literature:

1) "Chemistry of the Amino Acids" by J. P. Greenstein and M. Winitz, Wiley and Sons, Inc. New York, N.Y. (1961).

2) "Comprehensive Organic Transformations" by R Larock, VCH Publishers (1989).

3) T. D. Ocain and D. H. Rich, J. Med. Chem., 31, pp. 2193–2199 (1988).

4) E. M. Gordon, J. D. Godfrey, N. G. Delaney, M. M. Asaad, D. Von Langen, and D. W. Cushman, J. Med. Chem., 31, pp. 2199–2210 (1988).

5) "Practice of Peptide Synthesis" by M. Bodansky and A. Bodanszky, Springer-Verlag, New York, N.Y. (1984).

6) "Protective Groups in Organic Synthesis" by T. Greene and P. Wuts (1991).

7) "Asymmetric Synthesis: Construction of Chiral Molecules Using Amino Acids" by G. M. Coppola and H. F. Schuster, John Wiley and Sons, New York, N.Y. (1987).

8) "The Chemical Synthesis of Peptides" J. Jones, Oxford University Press, New York, N.Y. (1991).

9) "Introduction of Peptide Chemistry" by P. D. Bailey, John Wiley and Sons, New York, N.Y. (1992).

10) "Synthesis of Optically Active α-Amino Acids" by R. M. Williams, Pergamon Press, Oxford, U.K (1989).

11) S. Y. Tamura, B. M. Shamblin, T. K Brunck, and W. C. Ripka, Bioorganic & Medicinal Chemistry Letters, 7, pp. 1359–1364 (1997).

The following schemes depict the procedures set forth herein:

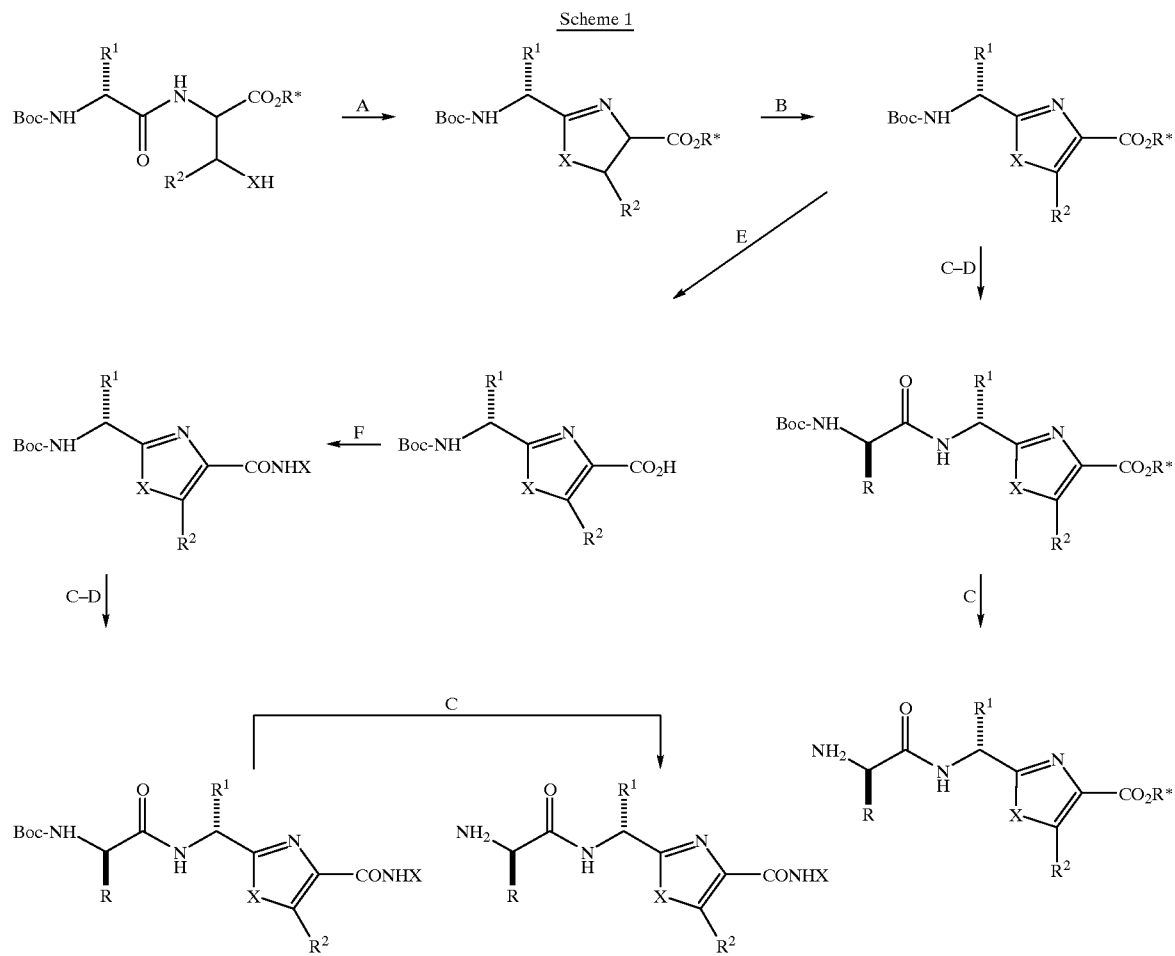
a) MeO$_2$CNSO$_2$N(C$_2$H$_5$)$_3$; b) HMTA, CuBr$_2$, DBU; c) CF$_3$CO$_2$H; d) Boc-amino acid, coupling agent; e) K$_2$CO$_3$, CH$_3$OH; f) amine, coupling agent
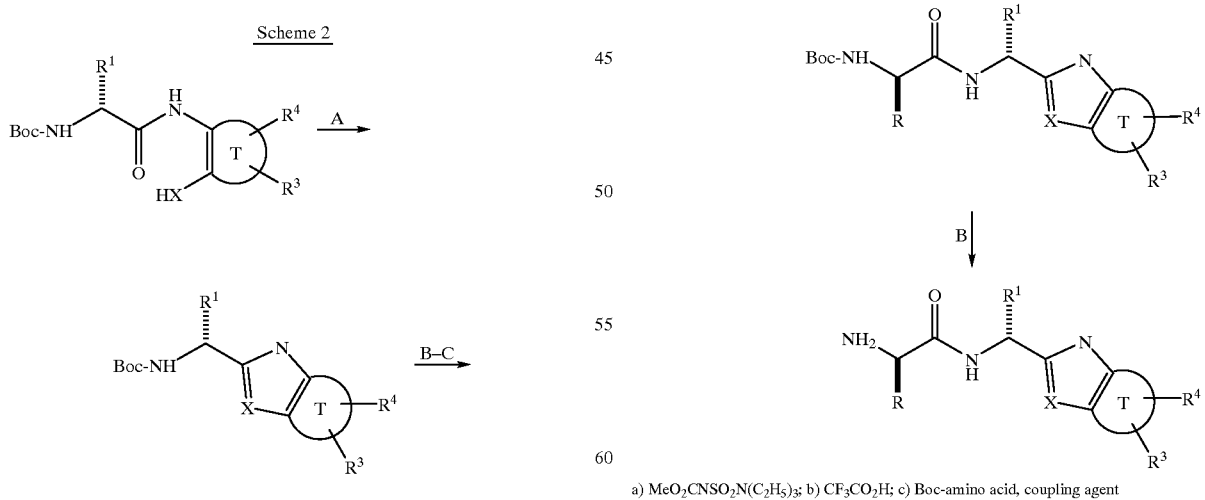
a) MeO$_2$CNSO$_2$N(C$_2$H$_5$)$_3$; b) CF$_3$CO$_2$H; c) Boc-amino acid, coupling agent

Scheme 3

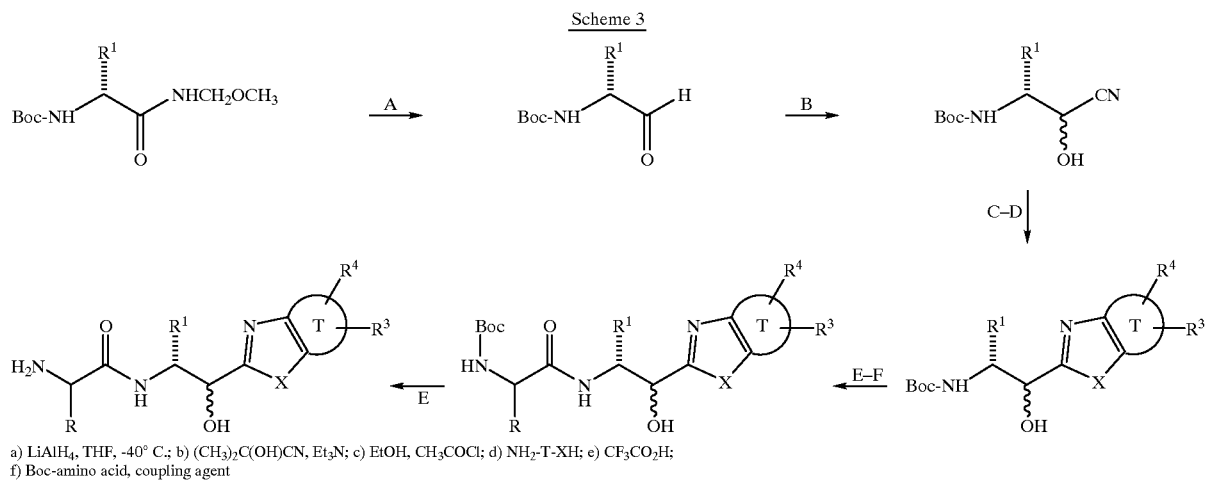

a) LiAlH₄, THF, -40° C.; b) (CH₃)₂C(OH)CN, Et₃N; c) EtOH, CH₃COCl; d) NH₂-T-XH; e) CF₃CO₂H;
f) Boc-amino acid, coupling agent

Scheme 4

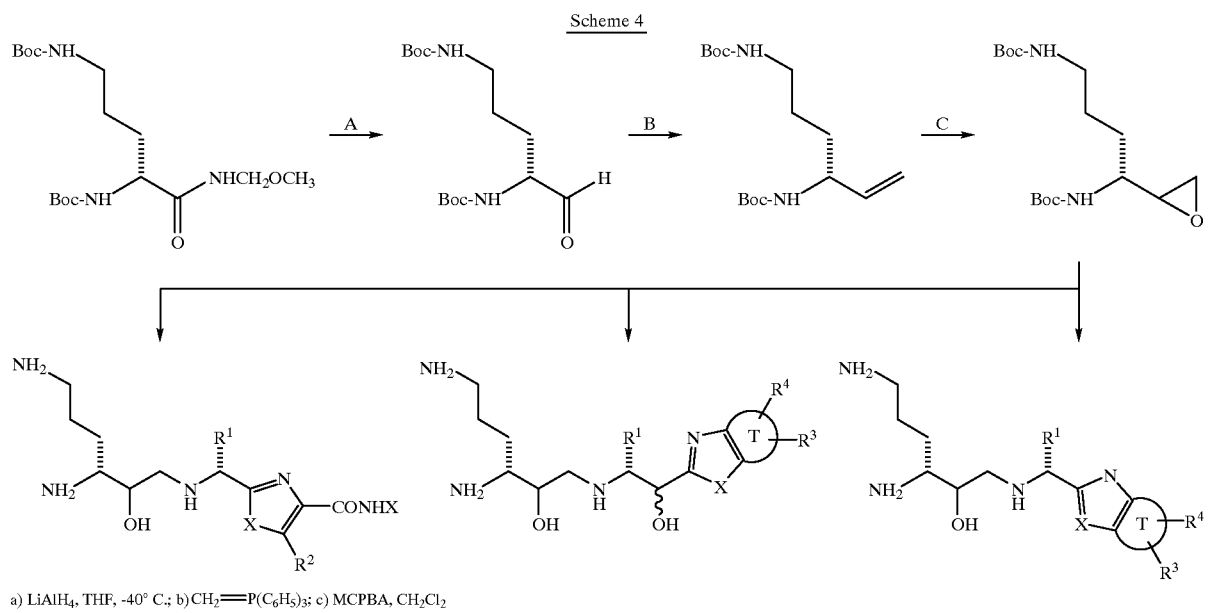

a) LiAlH₄, THF, -40° C.; b) CH₂=P(C₆H₅)₃; c) MCPBA, CH₂Cl₂

Compound 1 Ethyl 2-[(1R)-1-[(2R)-2,5-diaminovaleramido]-3-phenylpropyl]-4-oxazolecarboxylate Trifluoroacetate (A) N-Boc-D-homophenylalaine-L-serine Ethlyl Ester A cold (0° C.) solution of N-Boc-D-homophenylalanine (300 mg) in dichloromethane (10 mL), under nitrogen atmosphere, was treated sequentially with triethylamine (165 μL) and ethyl chlorofonmate (102 μL). After stirring for 2 h at 0 C., the crude mixed anhydride was added dropwise to a solution of L-serine ethyl ester hydrochloride (182 mg), triethylamine (300 μL), and dichloromethane (2 mL). The mixture is stirred at 0° C. for 1 h and then allowed to warm to 25 ° C. and stirred for 12 h. The reaction mixture is diluted with ethyl acetate, washed successively with water and brine, dried (Na₂SO₄) and concentrated. The residue was purified using chromatography over silica gel (50% ethyl acetate/hexane) to afford the title compound (371 mg): ¹H NMR (400 MHz, CDCl₃) δ1.32 (t, J=9.8 Hz, 3H), 1.46 (s, 9H), 1.97 (m, 1H), 2.11 (m, 1H), 2.75 (t, J=10.4 Hz, 2H), 3.97 (m, 2H), 4.14 (m, 1H), 4.25 (q, J=9.8 Hz, 2H), 4.60 (m, 1H), and 7.18–7.29 (m, 5H).

(B) Ethyl N-Boc-2-[(1R)-1-amino-3-phenylpropyl]-4-oxazolidenecarboxylate

A solution of N-Boc-D-homophenylalanine-L-serine ethyl ester (241 mg), anhydrous tetrahydrofuran (5 mL) and (methoxycarbonylsulfamoyl)tiethyl-ammonium hydroxide (Burgess reagent, 160 mg) is heated to reflux for 30 min. After cooling, the solution is diluted with ethyl acetate and washed successively with water and brine, dried (Na₂SO₄) and concentrated. The residue was purified by chromatography over silica gel (40% ethyl acetate/hexane) to afford the title compound (108 mg): ¹H NMR (400 MHz, CDCl₃) δ1.31 (t, J=8.2 Hz, 3H), 1.44 (s, 9H), 2.01 (m, 1H), 2.18 (m, 1H), 2.70 (m, 2H), 4.22 (m, 4H), 4.35 (dd, J=12.8; 12.5 Hz, 1H), 4.54 (m, 2H), 4.67 (dd, J=12.9; 11.2 Hz, 1H), 7.18 (m, 3H), and 7.26 (m, 2H).

(C) Ethyl N-Boc-2-[(1R)-1-amino-3-phenylpropyl]-4-oxazolecarboxylate

A cold solution (5° C.) of hexamethylenetetramie (HMTA) (258 mg), copper (II) bromide (256 mg) and 1,8-diazabicyclo[5.4.0]undec-7-ene (172 μL) and chloroform (2.5 mL) is treated dropwise (20 min) with a solution of ethyl N-Boc-2-[(1R)-1-amino-3-phenylpropyl]-4-oxazolidenecarboxylate (108 mg) in chloroform (5 mL). After stiring at 25° C. for 24 h, the reaction mixture is concentrated to a dark residue and is partitioned into ethyl acetatel $NH_4Cl:NH_4OH$ (1:1 mixture). The aqueous layer was extracted thrice with ethyl acetate and the combined organic layer is washed successively thrice with $NH_4Cl:NH_4OH$ (1:1), 10% citric acid, sat. sodium bicarbonate and brine. After diying ($Na_2SO_4$) and concentration in vacuo, the residue is purified by chromatography over silica gel (25% ethyl acetate/hexane) to give the title compound (48 mg) as a glassy solid: $^1H$ NMR (400 MHz, $CDCl_3$) δ1.39 (t, J=6.6 Hz, 3H), 1.44 (s, 9H), 2.17 (m, 1H), 2.29 (m, 1H), 2.68 (t, J=8.1 Hz, 2H), 4.40 (q, J=6.6 Hz, 2H), 4.96 (m, 1H), 5.24 (bs, 1H, NH), 7.18 (m, 3H), 7.25 (m, 2H), and 8.18 (s, 1H).

(D) Ethyl 2-[(1R)-1-[N'-Bis-Boc-(2R)-2,5-diaminovaleramido]-3-phentlpropyl]-4-oxazole-carboxylate A solution of ethyl N-Boc-2-[(1R)-1-amino-3-phenylpropyl]-4-oxazolecarboxylate (48 mg) and trifluoroacetic acid (1 mL) was stirred for 20 min. at 25° C. and concentrated in vacuo, with residual volatiles being removed by coevaporation with toluene. This intermediate is then coupled with the mixed anhydride, derived from N,N'-bis-Boc-D-omnithine (28 mg) and ethyl chloroformate, to afford the titled compound (69 mg) as a glassy solid: $^1H$ NMR (400 MHz, $CDCl_3$) δ1.38 (t, J=7.3 Hz, 3H), 1.41 (s, 9H), 1.44 (s, 9H), 1.58 (m, 2H), 1.86 (m, 2H), 2.21 (m, 1H), 2.36 (m, 1H), 2.70 (m, 2H), 3.09 (m, 1H), 3.29 (m, 1H), 4.39 (q, J=7.3 Hz, 2H), 4.80 (m, 1H), 5.11 (bs, 1H, NH), 5.24 (m, 1H), 7.18 (m, 3H), 7.27 (m, 2H), and 8.16 (s, 1H).

(E) Ethyl 2-[(1R)-1-[(2R)-2,5-diaminovalerado]-3-phenylpropyl]-4-oxazolecarboxmlate Trifluoroacetate A solution of ethyl 2-[(1R)-1-[(2R)-N,N'-bis-Boc-2,5-diaminovaleramido]-3-phenyl-propyl]-4-oxazole-carboxylate (67 mg) and trifluoroacetic acid (1 mL) was kept at 25° C. for 1 hr, concentrated in vacuo and coevaporated with toluene. The residue was purified further by reverse phase chromatography (20 mL Amberchrom, 0% to 50 % $CH_3CN$ in 0.1% aqueous TFA over 45 min. at 2 ml/min. flow-rate) to give the desired compound (60 mg) as a white powder: $^1H$ NMR (400 MHz, $D_2O$) δ1.41 (t, J=7.1 Hz, 3H), 1.80 (m, 2H), 2.02 (m, 2H), 2.39 (m, 1H), 2.46 (m, 1H), 2.80 (m, 1H), 2.87 (m, 1H), 3.10 (t, J=7.4 Hz, 2H), 4.17 (t, J=6.4 Hz, 1H), 4.43 (q, J=7.1 Hz, 2H), 5.14 (t, J=7.0 Hz, 1H), 7.32 (m, 3H), 7.41 (m, 2H), and 8.48 (s, 1H).

Compound 2—Benzyl-2-[(1R)-1-[(2R)-2,5-diamnovaleramido]-3-phenylpropyl]-4-oxazole-arboxylate Trifluoroacetate (A) N-Boc-D-homophenylalanine-L-serine Benzyl Ester This compound was prepared from N-Boc-D-homophenylalanine (500 mg) and L-serine benzyl ester hydrochloride (415 mg), with purification by chromatography over silica gel (40% ethyl acetate/hexane) to afford title compound (290 mg) as a glassy solid: $^1H$ NMR (400 Mz, $CDCl_3$) δ1.42 (s, 9H), 1.97 (m, 1H), 2.18 (m, 1H), 2.70 (m, 2H), 3.98 (m, 2H), 4.19 (m, 1H), 4.64 (m, 1H), 5.29 (bs, 2H), 7.16–7.29 (m, 5H), and 7.36 (bs, 5H).

(B) Benzyl N-Boc-2-[(1R)-1-amino-3-phenylpropyl]-4-oxazolidenecarboxylate

N-Boc-D-homophenylalanine-L-serine benzyl ester (290 mg) was converted to the title compound (136 mg), and purified by chromatography over silica gel (50% ethyl acetate/hexane) to give a glassy solid: $^1H$ NMR (400 MH, $CDCl_3$) δ1.43 (s, 9H), 2.01 (m, 1H), 2.18 (m, 1H), 2.70 (m, 2H), 4.34 (t, J=11.2 Hz, 1H), 4.55 (m, 2H), 4.72 (dd, J=11.3; 10.1 Hz, 1H), 5.19 (d, J=12.3 Hz, 1H), 5.22 (bs, 1H, NH), 5.23 (d, J=12.3 Hz, 1H), 7.19 (m, 3H), 7.25 (m, 2H), and 7.37 (m, 5H).

(C) Benzyl N-Boc-2-[(1R)-1-amino-3-phenylpropyl]-4-oxazolecarboxylate

Benzyl N-Boc-2-[(1R)-1-amino-3-phenylpropyl]-4-oxazolidenecarboxylate (236 mg) is dehydrogenated (cf., Compound 1-C) and purified by chromatography over silica gel (30% ethyl acetate/hexane) to afford title product (50 mg) as a glassy solid: $^1H$ NMR (400 MHz, $CDCl_3$) δ1.42 (s, 9H), 2.17 (m, 1H), 2.28 (m, 1H), 2.69 (m, 2H), 4.99 (m, 1H), 5.24 (m, 1H, NH), 5.39 (s, 2H), 7.19 (m, 3H), 7.26 (m, 2H), 7.40 (m, 5H), and 8.08 (s, 1H).

(D) Benzyl 2-[(1R)-1-[N,N'-Bis-Boc-(2R)-2,5-diaminovaleramido]-3-phenylpropyl]-4-oxazolecarboxylate A solution of benzyl N-Boc-2-[(1R)-1-amino-3-phenylpropyl]-4-oxazolecarboxylate (20 mg) and trifluoroacetic acid (1 mL) was stirred for 20 min. at room temperature and concentrated in vacuo, with residual volatiles being removed by coevaporation with toluene. The 2-[(1R)-1-amino-3-phenylpropyl]-4-oxazolecarboxylate is then coupled with the mixed anhydride, derived from N,N'-bis-Boc-D-ornithine (10 mg) and ethyl chloroformate, to afford title product (17 mg) as a glassy solid: $^1H$ NMR (400 MHz, $CDCl_3$) δ1.39 (s, 9H), 1.42 (s, 9H), 1.58 (m, 2H), 1.77 (m, 1H), 1.81 (m, 1H), 2.10 (m, 1H), 2.38 (m, 1H), 2.71 (m, 2H), 3.06 (m, 1H), 3.29 (m, 1H), 4.22 (bs, 1H, NH), 4.78 (rn, 1H), 5.10 (bs, 1H, NH), 5.25 (m, 1H), 5.38 (s, 2H), 7.19 (m, 3H), 7.23 (m, 2H), 7.39 (m, 5H), and 8.17 (s, 1H).

(E) Benzyl 2-[(1R)-1-[(2R)-2,5-diamiovaleramidol-3-phenylpropyl]-4-oxazolecarboxylate Trifluoroacetate Trifluoroacetic acid deprotection of benzyl 2-[(1R)-1-[N,N'-bis-Boc-(2R)-2,5-diaminovaleramido]-3-phenylpropyl]-4-oxazolecarboxylate (17 mg) afforded title product (18 mg) as a white powder: $^1H$ NMR (400 Mz, $D_2O$) δ1.79 (m, 2H), 2.02 (m, 2H), 2.41 (m, 2H), 2.79 (m, 1H), 2.86 (m, 1H), 3.06 (m, 2H), 4.18 (t, J=7.9 Hz, 1H), 5.16 (t, J=9.2 Hz, 1H), 5.42 (s, 2H), 7.22 (m, 3H), 7.37 (m, 2H), 7.58 (m, 5H), and 8.43 (s, 1H).

Compound 3—Benzyl 2-[(1R)-1-[(2R)-2,5-diaminovaleramido]-3-(2-naphthyl)-propyl]-4-oxazolecarboxylate Trifluoroacetate (A) N-Boc-D-2-naphthylalanine-L-serine Benzyl Ester.

Title compound (370 mg), obtained from N-Boc-D-2-naphthylalanine (500 mg) and L-serine benzyl ester hydrochloride (367 mg), is a glassy solid: $^1H$ NMR (400 MHz, $CDCl_3$) δ1.41 (s, 9H), 3.21 (dd, J=13.0; 9.6 Hz, 1H), 3.26 (dd, J=13.0; 7.3 Hz, 1H), 4.45 (m, 1H), 3.81 (m, 2H), 4.63 (m, 1H), 5.06 (bd, J=8.4 Hz, 1H, NH), 5.18 (s, 2H), 7.24 (bd, J=8.4 Hz, 1H, NH), 7.35 (m, 5H), 7.47 (m, 2H), 7.68 (s, 1H), and 7.81 (m, 4H).

(B) Benzyl N-Boc-2-[(1R)-1-amino-3-(2-naphthyl)propyl]-4-oxazolidene-carboxylate Dehydrative cyclization of N-Boc-D-2-naphthylalanine-L-serine benzyl ester (370 mg) afforded, after chromatography over silica gel (25% ethyl acetate/hexane), the title compound (210 mg) as a glassy solid: $^1H$ NMR (400 MHz, $CDCl_3$) δ1.42 (s, 9H), 3.23 (m, 1H), 3.35 (m, 1H), 4.42 (t, J=10.0 Hz, 1H), 4.57 (t, J=8.8 Hz, 1H), 4.69 (t, J=10.0 Hz, 1H), 4.83 (m, 1H), 5.12 (d, J=12.5 Hz, 1H), 5.14 (bs, 1H, NH), 5.21 (d, J=12.5 Hz, 1H), 7.36 (m, 5H), 7.43 (m, 21), 7.60 (s, 1H), and 7.78 (m, 4H).

(C) Benzyl N-Boc-2-[(1R)-1-amino-3-(2-naphthyl)propyl]-4-oxazolecarboxylate

Dehydrogenation of benzyl N-Boc-2-[(1R)-1-amino-3-(2-naphthyl)propyl]-4-oxazolidenecarboxylate (197 mg) afforded, after chromatography over silica gel (20% ethyl acetate/hexane), the title compound (55 mg) as a glassy solid: $^1$H NMR (400 MHz, CDCl$_3$) δ1.40 (s, 9H), 3.40 (m, 2H), 5.28 (m, 1H), 5.39 (s, 2H), 7.40 (m, 8H), 7.56 (s, 1H), 7.78 (m, 3H), and 8.12 (s, 1H).

(D) Benzyl 2-[(1R)-1-[N,N'-Bis-Boc-(2R)-2,5-diaminovaleramido]-3-(2-naphthyl)propyl]-4-oxazolecarboxylate A solution of benzyl N-Boc-2-[(1R)-1-amino-3-(2-naphthyl)propyl]-4-oxazole-carboxylate (54 mg) and trifluoroacetic acid (1 mL) was kept at room temperature for 30 min and concentrated in vacuo, with residual volatiles removed by coevaporation with toluene. The crude benzyl 2-[(1R)-1-amino-3-(2-naphthyl)propyl]-4-oxazole-carboxylate was then coupled with N,N'-bis-Boc-D-ornithine (29 mg) in dichloromethane (3 mL) in the presence of bromo-tris(pyrrolidino)phosphonium hexafluorophosphate (PyBrop, 80 mg) and triethylamine (100 μL) at 0 ° C. for 1 h. After stirring at 25 ° C. for 10 hrs, the reaction mixture is poured into ethyl acetate, washed successively with water, 1 N HCl, saturated aqueous bicarbonate and brine. The organic layer is dried (Na$_2$SO$_4$), concentrated and the residue is purified by chromatography over silica gel (30% ethyl acetate/hexane) affording the title compound (43 mg) as a glassy solid: $^1$H NMR (400 MHz, CDCl$_3$) δ1.39 (s, 18H), 1.42 (m, 3H), 1.73 (m, 1H), 2.96 (m, 1H), 3.16 (m, 1H), 3.40 (dd, J=13.0; 10.1 Hz, 1H), 3.48 (dd, J=13.0; 9.3 Hz, 1H), 4.18 (m, 1H), 4.59 (bs, 1H, NH), 4.99 (bs, 1H, NH), 5.37 (s, 2H), 5.60 (m, 1H), 7.39 (m, 7H), 7.58 (s, 1H), 7.78 (m, 4H), and 8.12 (s, 1H).

(E) Benzyl 2-[(1R)-1-[(2R)-2,5-diaminovaleramido]-3-(2-naphthyl)propyl]-4-oxazole-carboxylate Trifluoroacetate Trifluoroacetic acid-mediated deprotection of benzyl 2-[(1R)-1-[N,N'-bis-Boc-(2R)-2,5-diaminovaleramido]-3-(2-naphthyl)propyl]-4-oxazolecarboxylate (43 mg) afforded the title compound (40 mg) as a white powder: $^1$H NMR (300 MHz, D$_2$O) δ1.51 (m, 2H), 1.74 (m, 2H), 2.74 (m, 2H), 3.49 (m, 2H), 3.92 (t, J=6.2 Hz, 1H), 5.32 (s, 2H), 5.44 (t, J=8.1 Hz, 1H), 7.34 (m, 6H), 7.51 (m, 2H), 7.65 (s, 1H), 7.82 (m, 3H), and 8.41 (s, 1H).

Compound 4—2-[(1R)-1-[(2R)-2,5-Diaminovaleramido]-3-phenylpropyl]-N-(2-naphthyl)-4-oxazolecarboxamide Trifluoroacetate (A) N'-Boc-2-[(1R)-1-amino-3-phenylpropyl]-N-(2-naphthyl)-4-oxazolecarboxamide.

N-Boc-2-[(1R)-1-amino-3-phenylpropyl]oxazole-4-carboxylic acid (140 mg) and 2-naphthylamirne (58 mg) were coupled (EDAC-mediated) to afford the title compound (55 mg) as a white solid: $^1$H NMR (400 MHz, CDCl$_3$) δ1.48 (s, 9H), 2.21 (m, 1H), 2.36 (m, 1H), 2.74 (m, 2H), 5.02 (m, 1H), 5.18 (m, 1H, NH), 7.20 (m, 3H), 7.30 (m, 2H), 7.42 (t, J=7.6 Hz, 1H), 7.49 (t, J=7.6 Hz, 1H), 7.64 (d, J=7.7 Hz, 1H), 7.82 (m, 3H), 8.23 (s, 1H), 8.39 (s, 1H), and 8.80 (s, 1H, NH).

(B) 2-[(1R-1-[N,N'-Bis-Boc-(2R)-2,5-diaminovaleramido]-3-phenylpropyl]-N-(2-naphthyl)-4-oxazolecarboxamide A solution of N$^1$-Boc-2-[(1R)-1-amino-3-phenylpropyl]-N-(2-naphthyl)-4-oxazole-carboxamide (53 mg) and trifluoroacetic acid (1 mL) was kept at room temperature for 20 min. and concentrated in vacuo, with residual volatiles being removed by coevaporation with toluene. The crude 2-[(1R)-1-amino-3-phenyl-propyl]-N-(2-naphthyl)oxazole-carboxamide is then reacted with the mixed anhydride, obtained from N,N'-bis-Boc-D-ornithine (28 mg) and ethyl chloroformate, to afford the title compound (54 mg) as a white solid.

(C) 2-[(1R)-1-[(2R)-2,5-Diaminovaleramido]-3-phenylpropyl]-N-(2-naphthyl)-4-oxazolecarb-oxamide Trifluoroacetate The title compound (56 mg) was obtained from 2-[(1R)-1-[N,N'-Bis-Boc-(2R)-2,5-diaminovaleramido]-3-phenylpropyl]-N-(2-naphthyl)-4-oxazolecarboxamide (54 mg) as a white powder: $^1$H NMR (300 MHz, D$_2$O) δ1.68 (m, 2H), 1.94 (m, 2H), 2.31 (m, 2H), 2.69 (m, 1H), 2.80 (m, 1H), 2.96 (t, J=7.7 Hz, 2H), 4.03 (t, J=6.6 Hz, 1H), 5.04 (t, J=6.9 Hz, 1H), 7.26 (m, 5H), 7.49 (m, 3H), 7.83 (m, 3H), 8.03 (s, 1H), and 8.27 (s, 1H).

Compound 5—2-[(1R)-1-[(2R)-2,5-Diaminovaleranido]-3-phenylpropyl]-N-(3-quinolyl)-4-oxazolecarboxamide Trifluoroacetate (A) N-Boc-D-homophenylalanie-L-serine Methyl Ester N-Boc-D-homophenylalanine (1.0 g) was coupled with L-serine methyl ester hydrochloride (600 mg) with EDAC (892 mg) and triethylamine (650 μL) in methylene chloride (15 mL). After stirrng for 10 h., the reaction mixture is poured into ethyl acetate, washed successively with water, 1 N hydrochloric acid, sat aqueous bicarbonate and brine. The organic layer is dried (Na$_2$SO$_4$) and concentrated in vacuo to give the title compound (1.3 g) as a white solid: $^1$H NMR (400 MHz, CDCl$_3$) δ1.43 (s, 9H), 1.97 (m, 1H), 2.20 (m, 1H), 2.73 (m, 2H), 2.84 (m, 1H), 3.79 (s, 3H), 3.95 (m, 2H), 4.17 (m, 1H), 4.62 (m, 1H), 5.14 (bs, 1H, NH), 7.06 (bd, 1H, NH), 7.19 (m, 3H), and 7.28 (m, 2H).

(B) Methl N-Boc-2-[(1R)-1-amino-3-phenylpropyl]-4-oxazolidenecarboxylate

This compound is prepared from N-Boc-D-homophenylalanine-L-senne methyl ester by dehydrative cyclization: $^1$H NMR (400 MHz, CDCl$_3$) δ1.42 (s, 9H), 2.00 (m, 1H), 2.19 (m, 1H), 2.70 (m, 2H), 3.79 (s, 3H), 4.34 (t, J=9.5 Hz, 1H), 4.56 (m, 2H), 4.67 (dd, J=11.4; 9.5 Hz, 1H), 5.21 (bs, 1H, NH), 7.18 (m, 3H), and 7.26 (m, 2H).

(C) Methyl N-Boc-2-[(1R)-1-amino-3-phenylproopyl]-4-oxazolecarboxglate

This compound is prepared by dehydrogenation of methyl N-Boc-2-[(1R)-1-amino-3-phenylpropyl] oxazolidenecarboxylate: $^1$H NMR (400 MHz, CDCl$_3$) δ1.43 (s, 9H), 2.18 (m, 1H), 2.27 (m, 1H), 2.66 (t, J=9.9 Hz, 2H), 3.92 (s, 3H), 4.98 (m, 1H), 5.25 (m, 1H, NH), 7.18 (m, 3H), 7.25 (m, 2H), and 8.18 (s, 1H).

(D) N-Boc-2-[(1R)-1-amino-3-phenylpropyl]-4-oxazolecarboxylic Acid

A solution of methyl N-Boc-2-[(1R)-1-amino-3-phenylpropyl]4-oxazolecarboxylate (388 mg) and potassium carbonate (1.5 g) in 90% methanol/water (10 mL) is brought to gentle reflux for 40 min. The reaction mixture is cooled, water is added and extracted thrice with ethyl acetate. The aqueous layer is acidified to pH 3 and extracted three times with ethyl acetate. The combined organic layer is washed twice with brine, dried (Na$_2$SO$_4$) and concentrated. The crude title product (372 mg) was >95% pure by NMR: $^1$H NMR (400 MHz, CDCl$_3$) δ1.41 (s, 9H), 2.18 (m, 1H), 2.22 (m, 1H), 2.69 (m, 2H), 5.01 (m, 1H), 5.88 (bs, 1H, NH), 7.16 (m, 3H), 7.23 (m, 2H), and 8.01 (s, 1H).

(E) N-Boc-2-[(1R)-1-Amino-3-phenylpropyl]-N-(3-quinolyl)-4-oxazolecarboxamide

N-Boc-2-[(1R)-1-amino-3-phenylpropyl]-4-oxazolecarboxylic acid (161 mg) was coupled to 3-aminoquinoline mediated with EDAC to afford the title compound (50 mg) as a white solid: $^1$H NMR (400 MHz, CDCl$_3$) δ1.49 (s, 9H), 2.20 (m, 1H), 2.36 (m, 1H), 2.77 (m, 2H), 5.01 (m, 1H), 5.18 (m, 1H, NH), 7.20 (m, 3H), 7.31 (m, 2H), 7.58 (t, J=9.5 Hz, 1H), 7.66 (t, J=9.5 Hz, 1H), 7.84 (d, J=9.7 Hz, 1H), 8.08 (d, J=9.7 Hz, 1H), 8.27 (s, 1H), 8.87 (s, 1H), 8.92 (s, 1H), and 8.95 (s, 1H, NH).

(F) 2-[(1R)-1-[N,N'-Bis-Boc-(2R)-2,5-diaminovaleramido]-3-phenylpropyl]-N-(3-quinolyl)-4-oxazolecarboxamide A solution of N-Boc-2-[(1R)-1-amino-3-phenylpropyl]-N-(3-quinolyl)-4-oxazole-carboxamide (46 mg) and trifluoroacetic acid (1 mL) was kept at ambient temperature for 20 min. and concentrated in vacuo, with residual volatiles removed by coevaporation with toluene. The crude 2-[(1R)-1-amino-3-phenylpropyl]-N-(3-quinolyl)-4-oxazolecarboxamide is then coupled with the mixed anhydride, derived from N,N'-bis-Boc-D-ornithine (25 mg) and ethyl chloroformate, to afford the title product (66 mg) as a white solid: $^1$H NMR (400 MHz, CDCl$_3$) δ1.42 (bs, 18H), 1.62 (m, 3H), 1.94 (m, 1H), 2.14 (m, 1H), 2.38 (m, 1H), 2.78 (m, 2H), 3.16 (m, 2H), 4.41 (m, 1H, NH), 4.96 (m, 1H ), 5.23 (m, 1H, NH), 7.19 (m, 3H), 7.26 (m, 2H), 7.58 (t, J=9.7 Hz, 1H), 7.65 (t, J=9.5 Hz, 1H), 7.83 (d, J=9.6 Hz, 1H), 8.09 (d, J=9.5 Hz, 1H), 8.96 (s, 1H), 8.23 (s, 1H), 8.99 (s, 1H), and 9.04 (s, 1H, NH).

(G) 2-[(1R)-1-[(2R)-2,5-Diaminovaleramido]-3-phenylpropyl]-N-(3-quiolyl)-4-oxazole-carboxamide Trifluoroacetate 2-[(1R)-1-[N,N'-Bis-Boc-(2R)-2,5-diaminovaleramido]-3-phenylpropyl]-N-(3-quinolyl)4-oxazole-carboxamide (66 mg) was deprotected with trifluoroacetic acid to afford the title compound (68 mg) as a white powder: $^1$H NMR (400 MHz, D$_2$O) δ1.83 (m, 2H), 2.06 (m, 2H), 2.45 (m, 1H), 2.57 (m, 1H), 2.83 (m, 1H), 2.96 (m, 1H), 3.11 (t, J=8.3 Hz, 2H), 4.19 (t, J=6.0 Hz, 1H), 5.22 (t, J=7.4 Hz, 1H), 7.38 (m, 3H), 7.42 (m, 2H), 7.96 (t, J=9.0 Hz, 1H), 8.09 (t, J=9.0 Hz, 1H), 8.23 (m, 2H), 8.60 (s, 1H), 9.11 (s, 1H), and 9.48 (s, 1H).

Compound 6—2-[(1R)-1-[(2R)-2,6-Diaminohexanamido]-3-phenylpropyl]-N-(3-quinolyl)-4-oxazolecarboxamide Trifluoroacetate This compound was prepared, as described in Compound 5, except the starting materials were 2-[(1R)-1-amino-3-phenylpropyl]-N-(3-quinolylsoxazolecarbox-amide and N,N'-bis-Boc-D-lysine.

Compound 7—2-[(1R)-1-[(2R)-2,3-Diaminopropionamido]-3-phenylpropyl]-N-(3-quinolyl)-4-oxazolecarboxamide Trifluoroacetate This compound was prepared, as described in Compound 5, except the starting materials were 2-[(1R)-1-amino-3-phenylpropyl]-N-(3-quinolyl)-4-oxazolecarbox-amide and N,N'-bis-Boc-D-diaminopropionic acid.

Compound 8—2-[(1R)-1-[(2R)-2,5-Diaminovaleramido]-3-(2-thienyl)propyl]-N-(3-quinolyl)-4-oxazolecarboxamide Trifluoroacetate This compound was prepared, as described in Compound 5, except the starting materials were 2-[(1R)-1-amino-3-(2-thienyl)propyl]-N-(3-quinolyl)-4-oxazole-carboxamide and N,N'-bis-Boc-D-ornithine.

Compound 9—2-[(1R)-1-[(2R)-2,5-Diaminovaleramido]-3-(3-furyl)propyl]-N-(3-quinolyl)4-oxazolecarboxamide Trifluoroacetate This compound was prepared, as described in Compound 5, except the starting materials were 2-[(1R)-1-amino-3-(3-furyl)propyl]-N-(3-quinolyl)-4-oxazolecarboxamide and N,N'-bis-Boc-D-ornithine.

Compound 10—2-[(1R)-1-[(2R)-2,5-Diaminovaleramido]-3-(4-fluorophenyl) propyl]-N-(3-quinolyl)-4-oxazolecarboxamide Trifluoroacetate This compound was prepared, as described in Compound 5, except the starting materials were 2-[(1R)-1-amino-3-(4-fluorophenyl)propyl]-N-(3-quinolyl)-4-oxazolecarboxamide and N,N'-bis-Boc-D-ornithine.

Compound 11—2-[(1R)-1-[(2R)-2-Amino-5-(quanidino)valeramido]-3-(4-fluoro-phenyl)propyl]-N-3-quinolyl)-4-oxazolecarboxamide Trifluoroacetate This compound was prepared, as descnied in Compound 5, except the starting materials were 2-[(1R)1-amino-3-(4-fluorophenyl)propyl]-N-(3-quinolyl)-4-oxazolecarboxamide and N,N',N"-tri-Boc-D-arginine.

Compound 12—2-[(1R)-1-[(2R)-2-Amino-5-(guanidino)valeramido]-3-(4-fluoro-phenyl)propyl]-N-(6-ethyl-3-quinolyl)-4-oxazolecarboxamide Trifluoroacetate This compound was prepared, as described in Compound 5, except the starting materials were 2-[(1R)-1-amino-3-(4-fluorophenylpropyl]-N-(6-ethyl-3-quinolyl)-4-oxazolecarbox-amide and N,N',N"-tri-Boc-D-arginine.

Compound 13—2-[(1R)-1-[(2R)-2,5-Diaminovaleramido]-3-(4-fluoro-phenyl) propyl]-N-(6tert-butyl-3-quinolyl)-4oxazolecarboxamide Trifluoroacetate This compound was prepared, as described in Compound 5, except the starting materials were 2-[(1R)-1-amino-3-(4fluorophenyl)propyl]-N-(6-tert-butyl-3-quinolyl)-4-oxazole-carboxamide and N,N'-bis-Boc-D-ornithine.

Compound 14—2-[(1R)-1-[(2R)-2,4-Diaminobutyranido]-3-(4-fluorophenyl)-propyl]-N-(2-naphthyl)-4-oxazolecarboxamide Trifluoroacetate This compound was prepared, as descnbed in Compound 5, except the starting materials were 2-[(1R)-1-amino-3-(4fluorophenyl)propyl]-N-(2-naphthyl)-4-oxazolecarboxamide and N,N'-bis-Boc-D iaminobutyric acid.

Compound 15—2-[(1R)-1-[(2R)-2,4-Diaminobutyramido]-3-(2,4-difluorophenyl)-propyl]-N-(7-tert-butyl-3-quinoly)-4-oxazolecarboxamide Trifluoroacetate This compound was prepared, as described in Compound 5, except the starting materials were 2-[(1R)-1-ammino3-(2,-fluorophenyl)propyl]-N-(7-tert-butyl-3-quinolyl)-4-oxazole-carboxamide and N,N'-bis-Boc-D-diaminobutyric acid.

Compound 16—2-[(1R)-1-[(2R)-2,5-Diaminovaleramido]-3-phenylpropyl]-N-(4-methoxy-3-quinolyl)-4-oxazolecarboxamide Trifuoroacetate This compound was prepared, as described in Compound 5, except the starting materials were 2-[(1R)-1-amino-3-phenylpropyl]-N-(4-methoxy-3quiolyl)-4-oxazolecarboxamide and N,N'-bis-Boc-D-omithine.

Compound 17—2-[(1R)-1-(2R)-2,5-Diaminovaleramido]-3-phenylpropyl]-N-(4-methoxy-2-quinolyl)-4-oxazolecarboxamide Trifluoroacetate This compound was prepared, as described in Compound 5, except the starting materials were 2-[(1R)-1-amino-3-phenylpropyl]-N-(4-methoxy-2-quinolyl)-4-oxazolecarboxamide and N,N'-bis-Boc-D-onithine.

Compound 18—2-[(1R)-1-[(2R)-2,6-Diaminohexanoamido]-3-(3,5-difluoro-2-thienyl)propyl]-N-(6,7-dimethyl-3-quinolyl)-oxazolecarboxamide Trifluoroacetate This compound was prepared, as described in Compound 5, except the starting materials were 2-[(1R)-1-amino-3-(3, 5-difluoro-2-thienyl)propyl]-N-(6,7-dimethyl-3-quinolyl)-oxazolecarboxamide and N,N'-bis-Boc-D-lysine.

Compound 19—2-[(1R)-1-[(2R)-2,5-Diaminovaleramido]-3-methylpropyl]-N-3-quinolyl-4-oxazolecarboxamide Trifluoroacetate This compound was prepared, as described in Compound 5, except the starting materials were 2-[(1R)-1-amino-3-methylpropyl]-N-(3-quinolyl)-oxazolecarbox-amide and N,N'-bis-Boc-D-ornithine.

Compound 20—2-[(1R)-1-[(2R)-2,5-Diaminovaleramido]-3-methylpropyl]-N-(5-tert-butyl-3-quinolyl)-4-oxazolecarboxamide Trifloroacetate This compound was prepared, as described in Compound 5, except the starting materials were 2-[(1R)-1-amio-3-methylpropyl]-N-(5-tert-butyl-3-quinoly)-4-oxazolecarboxamide and N,N'-bis-Boc-D-onithine.

Compound 21—2-[(1R)-1-[(2R)-2,5-Diaminovaleramido]-3-methylpropyl]-N-(3-quinolyl)-4-imidazolecarboxamide Trifluoroacetate This compound was prepared, as described in Compound 5, except the starting materials were 2-[(1R)-1-amino-3-methylpropyl]-N-(3-quinolyl)-4-imidazolecarboxamide and N,N'-bis-Boc-D-omnithine.

Compound 22—2-[(1R)-1-[(2R)-2,5-Diamiinovaleramnido]-3-phenylpropyl]-N-(3-quinolyl-imidazolecarboxamide Trifluoroacetate This compound was prepared, as described in Compound 5, except the starting materials were 2-[(1R)-1-ainio-3-phenylpropyl]-N-(3-quinolyl)-4-imidazolecarbox-amide and N,N'-bis-Boc-D-orithine Compound 23—2-[(1R)-1-[(2R-)2,5-Diaminovaleramido]-3-methylpropyl]-N-(5-tert-butyl-3-quinolyl)-4-thiazolecarboxamide Trifluoroacetate This compound was prepared, as described in Compound 5, except the starting materials were 2-[(1R)-1-amino-3-methylpropyl]-N-(5-tert-butyl-3-quinolyl)-4-thiazolecarboxamide and N,N'-bis-Boc-D-ornithine Compound 24—2-[(1R)-1-[(2R)-2,4-Diaminobutyramido]-3-(4-fluorophenyl)-propyl]-N-(5-ethyl-3-quinoly)-4-thiazolecarboxamide Trifluoroacetate This compound was prepared, as described in Compound 5, except the starting materials were 2-[(1R)-1-amino-3-(4-fluorophenyl)propyl]-N-(5-ethyl-3-quinolyl)-4-thiazolecarbox-amide and N,N'-bis-Boc-D-diaminobutyric acid.

Compound 25—(2R)-2,5-Diamino-N-[(1R)-1-(2-benzothiazoly)-3-phenyl-propyl]valeramide Trifluoroacetate This compound was prepared, as described in Compound 5, except the starting materials were (1R)-1-(2-benzothiazolyl)-3-phenylpropylamine and N,N'-bis-Boc-D-omithine Compound 26—(2R)-2,5-Diamino-N-(1R)1-(5-benzyl-2-benzothiazolyl)-3-phenyl-propyl]valeramide Trifluoroacetate This compound was prepared, as described in Compound 5, except the starting materials were (1R)-1-(5-benzyl-2-benzothiazolyl)-3-phenylpropylamine and N,N'-bis-Boc-D-omithine Compound 27—(2R)-2,5-Diamino-N-[(1R)-1-(5-benzyl-2-benzoxazolyl)-3-methylbutyl]valeramide Trifluoroacetate This compound was prepared, as described in Compound 5, except the starting materials were (1R)-1-(5-benzyl-2-benzoxazolyl)-3-methylbutylamine and N,N'-bis-Boc-D-ormithine Compound 28—(2R)-2,5-Diamino-N-[(1R)-1-(5,6-dichloro-2-benzimida-zolyl)-3-(2,4-difluorophenyl)propyl] valeramide Trifluoroacetate This compound was prepared, as described in Compound 5, except the starting materials were (1R)-1-(5,6-dichloro-2-benzimidazolyl)-3-(2,4-difluorophenyl) propylamine and N,N'-bis-Boc-D-ornithine Compound 29—(2R)-2,6-Diamino-N-[(1R)-1-(5-benzyl-6-chloro-2-benzimida-zolyl)-3-phenylpropyl]hexanosinde Trifluoroacetate This compound was prepared, as described in Compound 5, except the starting materials were (1R)-1-(5-benzyl-6-chlorobenzimidazolyl)-3-phenylpropylamine and N,N'-bis-Boc-D-lysine.

Compound 30—(2R)-2,5-Diamino-N-[(1R)-1-(6-chloro-4,5-diethyl-2-benzimida-zolyl)-2-(2-thienyl)ethyl] valeramide Trifluoroacetate This compound was prepared, as described in Compound 5, except the starting materials were (1R)-1-(6-chloro4,5-diethyl-2-benzimidazolyl)-2-(2-thienyl) ethyllamine and N,N'-bis-Boc-D-omithine Compound 31—(2R)-2,5-Diamino-N-[(1R)-1-[(RS)-(2-benzoxazolyl)hydroxy-methyl]-3-phenylpropyl]valeramide Trifluoroacetate (A) N-Boc-D-homoohenylalanine Methoxymethylamide A mixture of Boc-D-homophenylalanine (3.0 g), methoxymethylamine hydrochloride (1.15 g), PyBrop (5 g), diisopropylethylamine (5.6 mL), and dichloromethane (10 mL) was stirred at 25° C. for 10 h., and the reaction mixture was poured into ethyl acetate and washed successively with water, 1N HCl, sat. sodium bicarbonate and brine. The combined extracts was dried ($Na_2SO_4$) and concentrated in vacuo. Further purification by chromatography over silica gel (45% ethyl acetate/hexane) afforded titled compound (6.76 g) as a white solid: $^1$H NMR (400 MHz, $CDCl_3$) δ1.46 (s, 9H), 1.85 (m, 1H), 2.04 (m, 1H), 2.72 (m, 2H), 3.17 (s, 3H), 3.63 (s, 3H), 4.69 (m, 1H), 5.25 (bd, 1H, NH), 7.20 (m, 3H), and 7.28 (m, 2H).

(B) N-Boc-D-Homophenylalaninal

A cold (−40° C.) solution of lithium aluminum hydride (25.2 mL of a 1M solution) in tetrahydrofiran (165 mL), under nitrogen, is treated with a solution of N-Boc-D-homophenylalanine methoxymethylamide (6.76 g) in tetrahydrofuran (20 mL) at such a rate as to keep the temperature between −36 to −38° C. After the addition, the temperature is allowed to rise to 7° C. after which the reaction mixture is cooled to −35° C. The mixture is quenched with 2.75 M $KHSO_4$ solution and the mixture is stirred for 1 h while warming to 25 ° C. The aqueous layer is separated and extracted thrice with ether. The combined organics are washed successively thrice with 10% citric acid, water, saturated bicarbonate and brine, dried ($MgSO_4$) and concentrated. The viscous clear residue solidifies under vacuum to give the title compound (5.32 g): $^1$H NMR (400 MHz, $CDCl_3$) δ1.47 (s, 9H), 1.88 (m, 1H), 2.22 (m, 1H), 2.71 (t, J=7.6 Hz, 2H), 4.24 (m, 1H), 5.18 (bd, 1H, NH), 7.20 (m, 3H), 7.27 (m, 2H), and 9.54 (s, 1H).

(C) N-Boc-(2RS, 3R)-3-Amino-2-hydroxy-5-phenylvaleronitrile

A solution of N-Boc-D-homophenylalaninal (2.62 g), acetone cyanohydrin (2,5 g), triethylamine (834 μL), and methylene chloride (25 mL) is stirred for 4 h at 24 ° C. under nitrogen atmosphere. The reaction mixture is concentrated in vacuo and the residue is disssolved in ether, washed five times with brine, dried ($MgSO_4$), concentrated and purified by chromatography over silica gel (25% ethyl acetate/hexane) to afford the title compound (2.0 g) as a clear oil: $^1$H NMR (400 MHz, $CDCl_3$, 1:1 mixture of diastereomers) δ1.48 (s, 9H), 1.93 (m, 2,5H), 2.70 (m, 1H), 2.19 (m, 0.5H), 2.79 (m, 1H), 3.68 (m, 0.5H), 3.89 (m, 0.5H), 4.50 (m, 0.5H), 4.58 (m, 0.5H), 4.68 (m, 0.5H), 4.92 (bd, 0.5H, NH), 5.11 (bd, 0.5H, NH), 7.21 (m, 3H), and 7.32 (m, 2H).

(D) (1R)-1-[(RS)-(2-Benzoxazolyl)hydroxymethyl]-3-phenylpropylamine

A cold (0° C.) solution of acetyl chloride (2.44 mL) and chloroform (2.5 mL) is treated dropwise with anhydrous ethanol (2.3 mL) over 15 min., under nitrogen atmosphere. Then a solution of N-Boc-(2RS, 3R)-3-amino-2-hydroxy-5-phenylvaleronitrile (331 mg) in chloroform (5.8 mL) is added at 0° C. and the mixture is stirred for 1 h. The solvent is removed in vacuo, while maintaining the temperature below 20° C., resulting in a white solid. A solution of the crude imidate, o-aminophenol (137 mg), and anhydrous ethanol (5.8 mL) was heated to reflux for 6 h and then concentrated in vacua. The residue was partitioned between ethyl acetate and 1 N NaOH, and the organic layer washed with brine, dried (Na$_2$SO$_4$), concentrated and purified further by chromatography over silica gel (5% methanol/dichloromethane) to give the desired product (62 mg) as a clear oil: mass spectrum (ES+) m/e 283.0 (M+1); $^1$H NMR (400 MHz, CDCl$_3$, 3:2 mixture of diastereomers) δ1.62 (m, 0.6H), 1.81 (m, 1H), 1.99 (m, 1H), 2.16 (m, 0.4H), 2.79 (m, 2H), 3.26 (m, 0.4H), 3.42 (m, 0.6H), 4.78 (d, J=2.0 Hz, 0.6H), 4.92 (d, J=1.7 Hz, 0.4H), 7.15–7.34 (m, 7H), 7.55 (m, 1H), and 7.72 (m, 1H).

(E) N,N'-Bis-Boc-(2R)-2,5-Diamino-N-[(1R)-1-[(RS)-(2-benzoxazolyl)hydroxy-methyl]-3-phenylpropyl]valeramide (1R)-1-[(RS-(2-benzoxazolyl)hydroxymethyl]-3-phenylpropylamine (62 mg) is coupled with N,N'-bis-Boc-D-omithine (51 mg) to afford the title compound (110 mg) as a glassy solid: $^1$H NMR (400 MHz, CDCl$_3$, 3:2 mixture of diastereomers) δ1.39–1.42 (2s, 18H), 1.58 (m, 3H), 1.86 (m, 2H), 2.09 (m, 1H), 2.67–2.78 (m, 1.6H), 2.92 (m, 0.4H), 2.96–3.22 (m, 2H), 4.07 (m, 0.4H), 4.18 (m, 0.6H), 4.59 (m, 1.4H), 4.78 (m, 0.6H), 5.04 (s, 1H), 5.14 (bd, 0.4H, NH), 5.26 (bd, 0.6H, NH), 7.09–7.37 (m, 7H), 7.50 (m, 1H), and 7.71 (m, 1H).

(F) (2R)-2,5-Diamino-N-[(1R)-1-[(RS)-(2-benzoxazolyl]hydroxymethyl-3-phenyl-propyl]valeramide Trifluoroacetate Deprotection of N,N'-bis-Boc-(2R)-2,5-diamino-N-[(1R)-1-[(RS)-(2-benzoxazolyl)-hydroxymethyl]-3-phenylpropyl]valeramide (110 mg), with trifluoroacetic acid, afforded the title compound (65 mg) as a white powder: mass spectrum (ES+) m/e 397.2 (M+1); $^1$H NMR (400 MHz, CDCl$_3$) δ1.55–1.86 (m, 4H), 1.94–2.27 (m, 2H), 2.83 (m, 3.4H), 3.09 (m, 0.61), 3.97 (m, 1H), 4.52 (m, 1H), 5.05 (d, J=8.8 Hz, 0.4H), 5.26 (s, 0.6H), 7.39 (m, 51), 7.54 (m, 2H), 7.75 (m, 1H), and 7.81 (m, 1H).

Compound 32—(2R)-2,5-Diamino-N-[(1R)-1-[(RS)-(5-ter-butyl-2-benzoxazolyl)hydroxymethyl]-3-phenylpropyl]valeramide Trifluoroacetate (A) N-Cbz-D-homophenylalanine Methoxymethylamide Cbz-D-homophenylalanine (1.96 g) was transformed to the title compound (1.3 g) as a white solid: 1H NMR (400 MHz, CDCl$_3$) δ1.92 (m, 1H), 2.06 (m, 1H), 2.68 (m, 1H), 2.77 (m, 1H), 3.18 (s, 3H), 3.62 (s, 3H), 4.78 (m, 1H), 5.11 (d, J=11.7 Hz, 1H), 5.16 (d, J=11.7 Hz, 1H), 5.68 (bd, 1H, NH), and 7.15–7.43 (m, 10H).

(B) N-Cbz-D-homophenylalaninal

Selective reduction of N-Cbz-D-homophenylalanine methoxymethylamide (1.32 g) with lithium aluminum hydride in tetrahydrofuran afforded the title compound (970 mg) as white crystals: $^1$H NMR (400 MHz, CDCl$_3$) δ1.96 (m, 1H), 2.30 (m, 1H), 2.76 (m, 2H), 4.37 (m, 1H), 5.18 (s, 2H), 5.39 (bs, 1H, NH), 7.17–7.41 (m, 10H), and 9.58 (s, 1H).

(C) N-Cbz-(2RS, 3R)-3-Amino-2-hydroxy-5-phenylvaleronitrile

This compound (760 mg) is prepared from N-Cbz-D-homophenylalaninal (970 mg): $^1$H NMR (400 MHz, CDCl$_3$, 3:2 mixture of diastereomers) δ1.96 (m, 1.4H), 2.17 (m, 0.6H), 2.66 (m, 1H), 2.78 (m, 1H), 3.79 (m, 0.6H), 3.96 (m, 0.4H), 4.37 (m, 0.6H), 4.52 (m, 0.4H), 4.58 (m, 0.6H), 4.64 (m, 0.4H), 5.09–5.23 (m, 3H), and 7.18–7.43 (m, 10H).

(D) N-CBz-(1R)-1-[(RS)-(5-tert-Buty-2-benzoxazol)hydroxymethyl]-3-phenyl-propylamine N-Cbz-(2RS, 3R)-3-amino-2-hydroxy-5-phenylvaleronitrile (346 mg), via the imidate salt, and 4-ter-butyl-2-aminophenol (194 mg) afforded the title product (360 mg) as a white solid: $^1$H NMR (400 MHz, CDCl$_3$, 3:2 mixture of diastereomers) δ1.43 (s, 9H), 1.79–2.11 (m, 2H), 2.65 (m, 0.6H), 2.79 (m, 1.4H), 4.17 (m, 0.6H), 4.22 (m, 0.4H), 4.38 (m, 0.6H), 4.49 (m, 0.4H), 4.99–5.18 (m, 3H), 5.42 (bd, 0.6H, NH), 5.56 (bd, 0.4H, NH), 7.09–7.41 (m, 12H), and 7.72 (m, 1H).

(E) (1R)-1-[(RS)-(5-tert-Butyl-2-benzoxazolyl)hydroxymethl]-3-phenylpropylamine

A mixture of N-CBz-(1R)-1-[(RS)-(5-tert-butyl-2-benzoxazolyl)hydroxymethyl]-3-phenylpropylamine (360 mg), anhydrous methanol (8 ml), and 10% palladium-on-charcoal (40 mg) was degassed, under reduced pressure, and then stirred vigorously under hydrogen atmosphere for 10 h. The mixture is filtered on a nylon pad (0.45 pm porosity) and concentrated in vacuo to afford the title product (210 mg) as a clear oil: $^1$H NMR (400 MHz, CDCl$_3$, 3:2 mixture of diastereomers) δ1.80–2.02 (m, 2H), 2.65–2.89 (m, 2H), 3.23 (m, 0.4H), 3.39 (m, 0.6H), 4.76 (d, J=1.8 Hz, 0.6H), 4.84 (d, J=2.4 Hz, 0.4H), 7.09 (m, 3H), 7.29 (m, 2H), 7.43 (m, 2H), and 7.76 (s, 1H).

(F) (2R)-2,5-Diamino-N-[((1R)-1-[(RS)-(5-tert-butyl-2-benzoxazolyl)hydrox-methyl]-3-phenylpropyl]valeramide Trifluoroacetate A mixture of (1R)-1-[(RS)-(5-tert-butyl-2-benzoxazolyl) hydroxymethyl]-3-phenyl-propylamine (108 mg), N,N'-bis-Boc-D-ornithine (130 mg), dichloromethane (3 mL), PyBrop (164 mg) and triethylamine (195 μL) was stirred at 0° C. for 1 h, then at 25° C. for 10 h. The reaction mixture is poured into ethyl acetate, washed successively with water, 1 N HCl, saturated aqueous bicarbonate and brine. The organic layer is dried (Na$_2$SO$_4$), concentrated and the residue is purified by chromatography over silica gel (30% ethyl acetate/ hexane) afforded N,N'bis-Boc-(2R)-2,5-diamino-N-[(1R)-1-[(RS)-(5-tert-butyl-2-benzoxazolyl)-hydroxymethyl]-3-phenylpropyl]-valeramide (130 mg) which was deprotected (trifluoroacetic acid) to give the title product (107 mg) as a white powder: $^1$H NMR (300 MHz, D$_2$O) δ1.35 and 1.26 (2s, 9H), 1.54 (m, 2H), 1.85–2.19 (m, 2H), 2.77 (m, 4H), 4.79 (m, 1H), 4.42 (m, 1H), 5.02 (s, 0.2H), 5.14 (d, J=3.3 Hz, 0.8H), 7.21–7.38 (m, 5H), and 7.78 (m, 1H).

Compound 33—(2R)-2,5-Diamino-N-[(1R)-1-[(RS)-(5,6-dimethyl-2-benzoxazolyl)hydroxymethyl]-3-phenylpropyl]valeramide Trifluoroacetate (A) N-Cbz-(1R)-1-[(RS)-(5,6-Dimethyl-2-benzoxazolyl) hydroxymethyl]-3-phenyl-propylamine Reaction of N-Cbz-(2RS, 3R)-3-amino-2-hydroxy-5-phenylvaleronitrile (832 mg), via the imidate salt, and 3,4-dimethyl-2-aminophenol (390 mg) afforded the title compound (452 mg) as a white solid: $^1$H NMR (400 MHz, CDCl$_3$, 3:2 mixture of diastereomers) δ1.79 (m, 1H), 2.00 (m, 1H), 2.59–2.81 (m, 2H), 4.31 (m, 1H), 4.96–5.18 (m, 3H), 5.37 (bd, 0.6H, NH), 5.46 (bd, 0.4H, NH), and 7.09–7.41 (m, 12H).

(B) (1R)-1-[(RS)-(5,6-Dimethyl-2-benzoxazol)hydroxymethyl]-3-phenyl-propylamine

N-Cbz-(1R)-1-[(RS)-(5,6-Dimethyl-2-benzoxazolyl) hydroxymethyl]-3-phenylpropyl-amine (452 mg) is deprotected to afford the title product (279 mg) as a clear oil: $^1$H NMR (400 Mz, CDCl$_3$, 3:2 mixture of diastereomers) δ1.83 (m, 1.4H), 1.98 (m, 0.61), 2.36 and 2.34 (2s, 6H), 2.70 (m, 1H), 2.82 (m, 1H), 3.24 (m, 0.4H), 3.38 (m, 0.6H), 4.74 (d, J=3.0 Hz, 0.6H), 4.86 (d, J=3.6 Hz, 0.4H), 7.13–7.28 (m, 6H), 7.43 (s, 0.6H), and 7.44 (s, 0.4H).

(C) N,N'-Bis-Boc-(2R-2,5-Diamino-N-[(1R)-1-[(RS)-(5,6-dimethyl-2-benzoxazolyl)hydroxy-methyl]-3-phenylpropyl]valeramide (1R)-1-[(RS)-(5,6-dimethyl-2-benzoxazolyl)hydroxymethyl]-3-phenylpropylamine (157 mg) is coupled with N,N'-bis-Boc-D-ornithine to afford the title compound (343 mg) as a white solid: $^1$H NMR (400 MHz, CDCl$_3$, 3:2 mixture of diastereomers) δ1.39–1.43 (bd, 19H), 1.43–1.64 (m, 4H), 1.83 (m, 1H), 2.38 (m, 6H), 2.61–3.21 (m, 4H), 4.08 (m, 1H), 4.59 (m, 1H), 5.02 (s, 1H), 5.18 (bd, 0.6H, NH), 5.28 (bd, 0.4H, NH), 7.12–7.35 (m, 6H), 7.41 (s, 0.4H), and 7.46 (s, 0.6H).

(D) (2R)-2,5-Diamino-N-[(1R)-1-[(RS)-(5,6-dimethyl-2-benzoxazolyl) hydroxymethyl]-3-phenylpropyl]valeramide Trifluoroacetate N,N'-Bis-Boc-(2R)-2,5-Diamino-N-[(1R)-1-[(RS)-(5,6-dimethyl-2-benzoxazolyl)-hydroxymethyl]-3-phenylpropyl]valeramide (343 mg) was deprotected to afford the title compound (300 mg) as a white powder: mass spectrum (ES+) m/e 425.3 (M+1); $^1$H NMR (NMR (300 MHz, D$_2$O, 3:2 diastereomeric mixture) δ1.64 (m, 4H), 2.18 (m, 1H), 2.29 (m, 1H), 2.46 (m, 6H), 2.85 (m, 4H), 3.98 (m, 1H), 4.52 (m, 1H), 5.02 (s, 0.4H), 5.22 (s, 0.6H), 7.32–7.49 (m, 5H), and 7.59 (m, 2H).

Compound 34—(2R)-2,5-Diamino-N-[(1R)-1-[(RS)-(chloro-2-benzoxazolyl)-hydroxymethyl]-3-phenylpropyl]valeramide Trilluoroacetate (A) N-Cbz-(1R)-1-[(RS)-(5-Chloro-2-benzoxazolyl)hydroxnmethyl]-3-phenylpropylamine Reaction of N-Cbz-(2RS, 3R)-3-amino-2-hydroxy-5-phenylvaleronitrile (324 mg), via the imidate salt, and 4-chloro-2-aminophenol (160 mg) afforded the title product (286 mg) as a white solid: mass spectrum (ES+) m/e $^{35}$Cl 473.2; $^{37}$Cl 475.2 M+23 (Na)); $^1$H NMR (400 Mz, CDCl$_3$, 7:3 mixture of diastereomers) δ1.65–1.88 (m, 2H), 2.80 (m, 2H), 4.30 (m, 1H), 4.99 (s, 0.6H), 5.03 (s, 0.4H), 5.09 (d, J=0.9 Hz, 0.6H), 5.18 (d, J=1.3 Hz, 1.2H), 5.26 (bd, 0.6H, NH), 5.39 (bd, 0.4H, NH), 7.11–7.44 (m, 12H), 7.63 (s, 0.6H), and 7.69 (s, 0.4H).

(B) (1R)-1-[(R)-(5-Chloro-2-benzoxazolyl)hydroxymethyl]-3-phenylpropylamine

N-Cbz-(1R)-1-[(RS)-(5-Chloro-2-benzoxazolyl)hydroxymethyl]-3-phenylpropylamine (286 mg), after treatment with trifluoroacetic acid, afforded the title product (59 mg) as a clear oil: $^1$H NMR (400 Mlz, CDCl$_3$, 7:3 mixture of diastereomers) δ2.02 (m, 1H), 2.18 (m, 1H), 2.90 (m, 2H), 3.82 (m, 0.3H), 3.95 (m, 0.7H), 4.63 (d, J=9.6 Hz, 0.7H), 5.22 (d, J=8.9 Hz, 0.31), 7.12–7.24 (m, 6H), 7.38 (m, 2H), 7.56 (m, 1H), and 7.77 (m, 1H).

(C) N,N'-Bis-Boc-(2R)-2,5-Diamino-N-[(1R)-1-[(RS)-(5-chloro-2-benzoxazolyl)hydroxymethyl]-3-phenylropl]valeramide (1R)-1-[(RS)-(5-Chloro-2-benzoxazolyl)hydroxymethyl]-3-phenylpropylamine (136 mg) was coupled with N,N'-bis-Boc-D-omithine to afford the title compound (150 mg) as a glassy solid: mass spectrum (ES+) m/e $^{35}$Cl 653.4, $^{37}$Cl 655.4 (M+23 (Na)); $^1$H NMR (400 MHz, CDCl$_3$, 7:3 mixture of diastereomers) δ1.40 (m, 18H), 1.62 (m, 4H), 1.90 (m, 2H), 2.74 (m, 2H), 3.03–3.23 (m, 2H), 4.09 (m, 0.3H), 4.19 (m, 0.7H), 4.58 (m, 0.7H), 4.69 (m, 0,3H), 5.03 (m, 0.7H), 5.20 (m, 0.3H), 7.11–7.23 (m, 6H), 7.37 (m, 2H), 7.53 (m, 1H), 7.68 (m, 0.3H), and 7.76 (m, 0.7H).

(D) (2R)-2,5-Diamino-N-[(1R)-1-[(RS)-(5-chloro-2-benzoxazolyl)hydroxtmethl]-3-phenyl-propyl]valeramide Trifluoroacetate The titled compound (131 mg) was obtained from N,N'-bis-Boc-(2R)-2,5-diamino-N-[(1R)-1-[(RS)-(5-chloro-2-benzoxazolyl)hydroxymethyl]-3-phenylpropyl]valeramide (150 mg) as a white powder: mass spectmm (ES+) m/e $^{35}$Cl 431.3, $^{37}$Cl 433.3 (M+1); $^1$H NMR (300 MHz, D$_2$O, 7:3 mixture of diastereomers) δ1.63 (m, 2H), 1.78 (m, 1H), 1.83 (m, 1H), 2.02 (m, 21H), 2.71–3.12 (m, 4H), 3.98 (m, 0.7H), 4.09 (m, 0.3H), 4.46 (m, 1H), 5.05 (d, J=5.4 Hz, 0.7H), 5.21 (d, J=2.6 Hz, 0.3H), 7.26–7.40 (m, 4H), 7.59 (m, 2H), 7.77 (m, 1H), and 7.82 (m, 1H).

Compound 35—(2R)-2,5-Diamino-N-[(1R)-1-[(RS)-(2-benziidazolyl)hydroxy-methyl]-3-phenylpropyl]valeramide Trifluoroacetate (A) N-Cbz-(1R)-1-[(RS)-(2-Benzimidazolyl)hydroxymethyl]-3-phenyylpropylamine Reaction of N-Cbz-(2RS, 3R)-3-amino-2-hydroxy-5-phenylvaleronitrile (820 mg), via the imidate salt, and 1,2-diaminobenzene dihydrochloride (508 mg) afforded the title compound (581 mg) as a white solid: mass spectrum (ES+) m/e 415.2 (M+1); $^1$H NMR (400 MHz, CDCl$_3$, 3:2 mixture of diastereomers) δ1.81–2.05 (m, 2H), 2.50–2.73 (m, 2H ), 4.18 (m, 1H), 4.99–5.12 (m, 3H), 5.46 (bd, 0.4H, NH), 5.74 (bd, 0.6H, NH), 7.02–7.32 (m, 13H), and 7.52 (m, 1H).

(B) N,N'-Bis-Boc-(2R)-2,5-Diamino-N-[(1R)-1-[(RS)-(2-benzimidazolyl)hydroxy-methyly]-3-phenylpropyl]valeramide N-Cbz-(1R)1-[(RS)-2-Benzimidazolyl)hydroxymethyl]-3-phenylpropylamine (581 mg) is deprotected in trifluoroacetic acid, and the residue is coupled to N,N'-bis-Boc-D-omithine to afford the title compound (110 mg): mass spectrum (ES+) m/e 596.3 (N+1); $^1$H NMR (400 Mz, CDCl$_3$, 3:2 mixture of diastereomers) δ1.46 (m, 9H), 1.42 (s, 9H), 1.58 (m, 4H), 2.02 (m, 2H), 2.63 (m, 2H), 2.82 (m, 2H), 3.18 (m, 1H), 4.16 (m, 1H), 4.49 (m, 1H), 5.17 (m, 1H), 5.42 (m, 11H), 7.03–7.23 (m, 8H), and 7.57 (m, 1H ).

(C) (2R)-2,5-Diamino-N-[(1R)-1-[(RS)-(2-benzimidazolyl)hydroxymethyl]-3-phenyl-propyl]valeradmide Trifluoroacetate Trifluoroacetic acid-mediated deprotection of N,N'-bis-Boc-(2R)-2,5-diamino-N-[(1R)-1-[(RS)-(2-benzimidazolyl)hydroxymethyl]-3-phenylpropyl]valeramide (110 mg) afforded two partially separable diastereomeric products A (39 mg) and B (56 mg) both as white powders. Diastereomer A: $^1$H NMR (300 MHz, D$_2$O) δ1.22 (m, 3H), 1.52 (m, 1H), 2.09 (m, 2H), 2.36 (m, 1H), 2.54 (m, 1H), 2.77 (m, 2H), 3.83 (t, J=5.8 Hz, 2H ), 4.52 (m, 1H), 5.34 (d, J=2.9 Hz, 1H), 7.35 (m, 5H), 7.50 (m, 2H), and 7.72 (m, 2H). Diastereomer B: mass spectrum (ES+) m/e 396.2 4(M+1); $^1$H NMR (300 Mz, D$_2$O, 3:2 mixture of B and A diastereomers) δ1.21 (m, 1H), 1.55 (m, 1H), 1.78 (m, 2H), 1.83–2.11 (m, 2H), 2.36 (m, 0.4H), 2.56 (m, 0.6H), 2.77 (m, 2H), 3.03 (m, 0.6H), 3.83 (t, J=5.8 Hz, 2H), 3.96 (t, J=6.6 Hz, 0.6H), 4.29 (m, 0.6H), 4.52 (m, 0.4H), 5.13 (d, J=5.5 Hz, 0.6H), 5.34 (d, J=2.9 Hz, 0.4H), 7.35 (m, 5H), 7.50 (m, 2H), and 7.72 (m, 2H).

Compound 36—(2R)-2,5-Diamino-N-[(1R)-1[(RS)-(1-oxazolo[4,5-b]pyridin-2-yl)-hydroxymethyl]-3-phenylpropyl]valeramide Trifluoroacetate (A) N-CBz-(1R)-1-[(RS)-(1-oxazolo[4,5-b]pyridin-2-yl)hydroxymethyl]-3-phenyl-propylamine Condensation of N-Cbz-(2RS, 3R)-3-amino-2-hydroxy-5-phenylvaleronitrile (343 mg), via the imidate salt, and 2-amino-3-hydroxypyridine (129 mg) afforded the title compound (180 mg) as a white solid: $^1$H NMR (400 M&z, CDCl$_3$, 3:2 mixture of diastereomers) δ1.82 (m, 1H), 1.99 (m, 1H), 2.60–2.86 (m, 2H), 4.38 (m, 1H), 4.66 (d, J=12,5 Hz, 0.6H), 4.82 (d, J=12,5 Hz, 0.6H), 5.17 (m, 1.8H), 5.78 (bd, 0.4H, NH), 6.22 (bd, 0.6H, NH), 6.69–7.37 (m, 11H), 7.74 (d, J=8.8 Hz, 0.4H), 7.79 (d, J=8.3 Hz, 0.6H), 8.47 (d, J=4.8 Hz, 0.6H), and 8.54 (d, J=4.1 Hz, 0.4H).

(B) (1R)-1-[(RS)-(1-Oxazolo[4,5-b]pyridin-2-yl)hydroxymethyl]-3-phenylpropylamine Deprotection of N-CBz-(1R)-1-[(RS)-(1-oxazolo[4,5-b]pyridin-2-yl)hydroxy-methyl]-3-phenylpropylamine (180 mg) afforded the product (51 mg) as a clear oil: $^1$H NMR (400 Mz, CDCl$_3$, 3:2 mixture of diastereomers) δ1.79–2.04 (m, 2H), 2.66–2.83 (m, 2H), 4.44 (m, 0.4H), 3.58 (m, 0.6H), 4.93 (d, J=1.6 Hz, 0.6H), 5.07 (d, J=2.6 Hz, 0.4H), 7.09–7.31 (m, 6l), 7.80 (d, J=7.5 Hz, 1H), and 8.53 (d, J=4.1 Hz, 1H).

(C) N,N'-Bis-Boc-(2R)-2,5-diamino-N-[(1R)-1-[(RS)-(1-oxazolo[4,5-b]pyridin-2-yl)-hydroxymethtl]-3-pheylpropyl]valeramide This titled compound (25 mg) is prepared from (1R)-1-[(RS)-(1-oxazolo[4,5-b]pyridin-2-yl)-hydroxy-methyl]-3-phenylpropylamine (42 mg): $^1$H NMR (400 MHz, CDCl$_3$, 3:2 mixture of diastereomers) δ1.38–1.42 (m, 18H), 2.77 (m, 2H), 1.89–1.96 (m, 2H), 2.11–2.23 (m, 2H), 2.62–2.83 (m, 2H), 2.96–3.19 (m, 2H), 4.19 (m, 1H), 4.80 (m, 1H), 5.11 (m, 1H), 7.11–7.32 (m, 6H), 7.83 (m, 1H), and 8.67 (m, 1H).

(D) (2R)-2,5-Diamino-N-[(1R)-1-[(RS)-(1-oxazolo[4,5-b]pyridin-2-yl)hydroxymethyl]-3-pheynylpropyl]-valeramide Trifluoroacetate N,N'-Bis-Boc-(2R)-2,5-diamino-N-[(1R)-1-[(RS)-(1-oxazolo[4,5-b]pyridin-2-yl)hydroxy-methyl]-3-phenylpropyl]valeramide (25 mg), after deprotection with trifluoroacetic acid, afforded the title product (20 mg) as a white powder: mass spectrum (ES+) m/e 398.3 (M+1); $^1$H NMR (400 MHz, CDCl$_3$, 3:2 mixture of diastereomers) δ1.69 (m, 4H), 1.92–2.21 (m, 2H), 2.73 (m, 2H), 3.00 (m, 2H), 3.99 (m, 1H ), 4.4 (m, 1H), 5.03 (d, J=6.2 Hz, 0.4H), 5.21 (d, J=2.6 Hz, 0.6H), 7.25 (m, 4H), 7.51 (m, 2H), 7.82 (m, 1H ), 8.13 (m, 1H), and 8.52 (m, 1H).

Compound 37—(2R)-2,5-Diamino-N-[(1R)-1-[(RS)-(2-benzothiazolyl)hydroxy-methyl]-3-phenylpropyl]valeramide Trifluoroacetate (A) (1R)-1-[(RS)-(2-Benzothiazolyl)hydroxymethyl]-3-phenylpropylamine Reaction of N-Cbz-(2RS, 3R)-3-amino-2-hydroxy-5-phenylvaleronitrile (690 mg), via the imidate salt, and 2-aminothiophenol (280 mg) afforded N-Cbz-(1R)-1-[(RS)-(2-benzothiazolyl)hydroxymethyl]-3-phenylpropylamine which was deprotected with trifluoroacetic acid to afford the title product (72 mg) as a white solid. While the diastereomers are partially separable by flash chromatography, the mixture was used in the subsequent reaction. Diastereomer A: $^1$H NMR (400 MHz, CDCl$_3$) δ2.83 (m, 2H ), 3.44 (m, 1H), 4.89 (d, J=1.1 Hz, 1H), 7.21 (m, 5H), 7.39 (t, J=8.7 Hz, 1H), 7.43 (t, J=10.5 Hz, 1H), 7.82 (d, J=8.7 Hz, 1H ), and 7.79 (d, J=10.6 Hz, 1H). Diastereomer B: $^1$H NMR (400 MHz, CDCl$_3$) δ2.21 (m, 2H), 2.79 (m, 2H ), 3.91 (m, 1H ), 5.39 (d, J=6.6 Hz, 1H), 7.18 (m, 3H), 7.23 (m, 2H), 7.39 (t, J=8.7 Hz, 1H), 7.43 (t, J=10.5 Hz, 1H), 7.82 (d, J=8.7 Hz, 1H), and 7.79 (d, J=10.6 Hz, 1H).

(B) N,N'-Bis-Boc-(2R)-2,5-Diamino-N-[(1R)-1-[(RS)-(2-benzothiazolyl)hydroxymethyl]-3-phenylpropyl]valeramide (1R)-1-[(RS)-(2-Benzothiazolyl)hydroxymethyl]-3-phenylpropylamine (72 mg) was coupled to N,N'-bis-Boc-D-ornithine to afford the title compound (11 mg) as a glassy solid: $^1$H NMR (400 MHz, CDCl$_3$, 3:2 mixture of diastereomers) δ1.41 (s, 9H), 1.44 (s, 9H), 1.60 (m, 2H ), 1.19 (m, 4H), 2.20 (m, 2H), 2.72–2.91 (m, 2H), 4.11 (m, 1H), 4.31 (m, 0.4H), 4.41 (m, 0.6H), 5.06 (m, 0.6H), 5.19 (d, J=1.1 Hz, 0.4), 7.20 (m, 3H), 7.26 (m, 2H), 7.40 (t, J=8.5 Hz, 1H), 7.49 (t, J=9.3 Hz, 1H), 7.87 (d, J=8.3 Hz, 1H ), and 7.98 (d, J=9.4 Hz, 1H).

(C) (2R)-2,5-Diamino-N-[(1R)-1-[((RS)-(2-benzothiazolyl)hydroxymethyl]-3-phenylpropyl]-valeramide Trifluoroacetate This compound is prepared from N,N'-bis-Boc-(2R)-2,5-diamino-N-[(1R)-1-[(RS)-(2-benzothiazolyl)hydroxymethyl]-3-phenylpropyl]valeramide:mass spectrum (ES+) m/e 413.3 (M+1); $^1$H NMR (300 MHz, D$_2$O, 7:3 mixture of diastereomers) δ1.75 (m, 2H), 1.92 (m, 2H), 2.09 (m, 2H), 2.66 (m, 2H), 2.99 (t, J=7.7 Hz, 2H), 3.88 (t, J=6.4 Hz, 0.3H), 3.98 (t, J=6.6 Hz, 0.7H), 4.18 (m, 0.3H), 4.31 (m, 0.7H), 5.22 (d, J=4.4 Hz, 0.7H), 5.29 (d, J=2.9 Hz, 0.3H), 7.20–7.38 (m, 5H), 7.50 (t, J=8.1 Hz, 0.7H), 7.58 (t, J=7.3 Hz, 0.7H), 7.70 (t, J=8.4 Hz, 0.3H), 7.81 (t, J=7.4 Hz, 0.3 H), 7.76 (d, J=7.8 Hz, 0.3H), 7.98 (d, J=7.7 Hz, 0.7H), 8.03 (d, J=8.4 Hz, 0.7H), and 8.09 (d, J=8.3 Hz, 0.3H).

Compound 38—(2R)-2,5-Diamio-N-[(1R)-1-[(RS)-(5,6-dimethyl-1-oxazolo[4,5-b]-pyridin-2-yl)hydroxymethyl]-3-phenylpropyl]valeramide Trifluoroacetate This compound was prepared, as described in Compound 36, except the starting materials were [(1R)-1-[(RS)-(5,6-dimethyl-1-oxazolo[4,5-b]pyridin-2-yl)hydroxymethyl]-3-phenylpropylamine and N,N'-bis-Boc-D-omithine.

Compound 39—(2R)-2,5-Diamino-N-[(1R)-1-[(RS)-(1-oxazolo[4,5c]pyridin-2-yl)-hydroxymethyl]-3-(4-fluorophenyl)propyl]valerade Trifluoroacetate This compound was prepared, as described in Compound 36, except the starting materials were [(1R)-1-[(RS)-(1-oxazolo[4,5-]pyridin-2-yl)hydroxymethyl]-3-(4-fluorophenyl)-propylamine and N,N'-bis-Boc-D-omithine.

Compound 40—(2R)-2,5-Diamino-N-[(1R)-1-[(RS)-(5benzyl-2-benzoxazolyl) hydroxymethyl]-3-(4-fluorophenyl)propyl]valermade Trifluoroacetate This compound was prepared, as described in Compound 31, except the startng materials were [(1R)-1-[(RS)-(5-benzyl-2-benzoxazolyl)hydroxymethyl]-3-(4-fluorophenyl)-propylamine and N,N'-bis-Boc-D-ortiibine.

Compound 41—(2R)-2,6-Diamino-N-[(1R)-1-[(RS)-(5-benzyl-2-benzoxazolyl) hydroxymethyl]-3-(4-fluorophenyl)propyl]hexanoamide Trifluoroacetate This compound was prepared, as described in Compound 31, except the starting materials were [(1R)-1-[(RS)-(5-benzyl-2-benzoxazolyl)hydroxymethyl]-3-(4-fluorophenyl)-propylamine and N,N'-bis-Boc-D-lysine.

Compound 42—(2R)-2,6-Diamino-N-[(1R)-1-[(RS)-(5, 6dimethyl-2-benzimidazolyl)-hydroxymethyl-3-(2,4-difluorophenyl)propyl]hexanoamide Trifluoroacetate This compound was prepared, as described in Compound 35, except the starting materials were [(1R)-1-[(RS)-(5,6-dimethyl-2-benzimidazolyl)hydroxymethyl]-3-(2,4-difluoro-phenyl)propylamine and N,N'-bis-Boc-D-lysine Compound 43—(2R)-2,5-Diamino-N-[(1R)-1-[(RS)-(1-methyl-2-benzimidazolyl)-hydroxymethyl]-3-(3-thienyl)propyl]valeramide Trifinoroacetate This compound was prepared, as described in Compound 35, except the starting materials were [(1R)-1-[(RS)-(1-methyl-2-benzimidazolyl)hydroxymethyl]-3-(3-thienyl)propyl-amine and N,N'-bis-Boc-D-ornithine Compound 44—(2R)-2,5-Diamino-N-[(1R)-1-[(RS)-(1, 6-dimethyl-2-benzimidazoly)-1-hydroxymethyl]-3-phenylpropyl]valeramide Trifluoroacetate This compound was prepared, as described in Compound 35, except the starting materials were [(1R)-1-[(RS)-(1,6-idnethyl-2-benzimidazolyl)hydroxymethyl]-3-phenylpropyl-amine and N,N'-bis-Boc-D-omithine Compound 45—(2R)-2,3-Diamino-N-[(1R)-1-[(RS)-4,5-dimethyl-2-benzoxazol)hydroxymethyl]-3-phenylpropyl]propionamide Trifluoroacetate This compound was prepared, as described in Compound 31, except the starting materials were [(1R)-1-[(RS)-(4,5-dimethyl-2-benzoxazolyl)hydroxymethyl]-3-phenylpropylamine and N,N'-bis-Boc-D-diaminopropionic acid.

Compound 46—(2R)-2,5-Diamino-N-[(1R)-1-[(RS)-(5,6-dimethyl-2-benzoxazol)hydroxymethyl]-3-phenylpropyl]valeramide Trifluoroacetate This compound was prepared, as described in Compound 31, except the starting materials were [(1R)-1-[(RS)-(5,6-dimethyl-2-benzoxazolyl)hydroxymethyl]-3-phenylpropylamie and N,N'-bis-Boc-D-ornithie.

Compound 47—(22)-2,4-Diamino-N-[(1R)-1-[(RS)-(5-phenyl-2-benzoxazolyl)-hydroxymethyl]-2-(4-fluorophenyl)ethyl]butyramide Trifluoroacetate This compound was prepared, as described in Compound 31, except the starting materials were [(1R)-1-[(RS)-(5-phenyl-2-benzoxazolyl)hydroxymethyl]-2-(4-fluorophenyl)ethyl-amine and N,N'-bis-Boc-D-dianinobutyric acid.

Compound 48—(2R)-2,6-Diamino-N-[(1R)-1-[(RS)-(5-phenoxy-2-benzoxazolyl)-hydroxymethyl]-3-phenylpropyl]hexanoamide Trifluoroacetate This compound was prepared, as described in Compound 31, except the starting materials were [(1R)-1-[(RS)-(5-phenoxy-2-benzoxazolyl)hydroxymethyl]-3-phenylpropylamine and N,N'-bis-Boc-D-lysine.

Compound 49—(2R)-2-Amino-5-goanidino-N-[(1R)-1-[(RS)-(5,6-dimethyl-2-benzoxazolyl)hydroxymethyl]-3-phenylpropyl]valeramide Trifluoroacetate This compound was prepared, as described in Compound 31, except the starting materials were [(1R)-1-[(RS)-(5,6-dimethyl-2-benzoxazolyl)hydroxymethyl]-3-phenylpropylamine and N,N',N''-tri-Boc-arginine.

Compound 50—(2R)-2-Amino-5-guanidino-N-[(1R)-1-[(RS)-(5-benzyl-2-benzimidazolyl)hydroxymethyl]-3-phenylpropyl]valeramide Trifluoroacetate This compound was prepared, as described in Compound 35, except the starting materials were [(1R)-1-[(RS)-(5-benzyl-2-benzimidazolyl)hydroxymethyl]-3-phenylpropylamine and N,N',N''-tri-Boc-arginine.

Compound 51—(2R)-2,5-Diamino-N-[(1R)-1-[(RS)-(5,6dimethyl-2-benzoxazolyl)hydroxymethyl]-3-methylbutyl]valeramide Trifluoroacetate This compound was prepared, as described in Compound 31, except the starting materials were [(1R)-1-[(RS)-(5,6-dimethyl-2-benzoxazolyl)hydroxymethyl]-3-methylbutylamine and N,N'-bis-Bocornithine.

Compound 52—(2R)-2,5-Diamino-N-[(1R)-1-[(RS)-(5,6dimethyl-2-benzimidazolyl)hydroxymethyl]-3-methylbutyl]valeramide Trifluoroacetate This compound was prepared, as described in Compound 35, except the starting materials were [(1R)-1-[(RS)-(5,6-dimethyl-2-benzimidazolyl)hydroxymethyl]-3-methylbutylamine and N,N'-bis-Boc-omithine.

Compound 53—(2R)-2,6-Diamino-N-[(1R)-1-(RS)-(6,7dimethyl-2-benzimidazolyI)-hydroxymethyl]-3-methylbutyl]valeramide Trifluoroacetate This compound was prepared, as described in Compound 35, except the starting materials were [(1R)-1-[(RS)-(6,7-dimetlhyl-2-benzoxazolyl)hydroxymethyl]-3-methylbutylamine and N,N'-bis-Boc-lysine.

Compound 54—(2R)-2,3-Diamino-N-[(1R)-1-[(RS)-(5-phenoxy-2-benzoxazolyo)-hydroxymethyl]-3-methylbutyl]propionamide Trifluoroacetate This compound was prepared, as described in Compound 31, except the starting materials were [(1R)-1-[(RS)-(5-phenoxy-2-benzoxazolyl)hydroxymethyl]-3-methylbutylamine and N,N'-bis-Boc-diaminopropionic acid.

Compound 55—(2R)-2,5-Diamno-N-[(1R)-1-[(RS)-(6-cyclopropyl-2-benzoxazolyl)-hydroxymethyl]-3-methylbutyl]valeramide Trifluoroacetate This compound was prepared, as described in Compound 31, except the starting materials were [(1R)-1-[(RS)-(6cyclopropyl-2-benzoxazolyl)hydroxymethyl]-3-methylbutylamine and N,N'-bis-Boc-oritbine.

Compound 56—(2R)-2,6-Diamno-N-[(1R)-1-[(RS)-(5-tert-butyl-2-benzoxazolyl)-hydroxymethyl]-3-methylpentyl]hexanoamide Trifluoroacetate This compound was prepared, as described in Compound 31, except the starting materials were [(1R)-1-[(RS)-(5-tert-butyl-2-benzoxazolyl)hydroxymethyl]-3-methylpentylamine and N,N'-bis-Boc-lysine.

Compound 57—(2R)-2-Amino-5-guanidino-N-1-(1R)-1-[(RS)-(5-phenoxy-2-benzoxazolyl)hydroxymethyl]-3-methylbutyl]valeramide Trifluoroacetate This compound was prepared, as described in Compound 31, except the starting materials were [(1R)-1-[(RS)-(5-phenoxy-2-benzoxazolyl)hydroxymethyl]-3-methylbutylamine and N,N'''-tri-Boc-arginie.

Compound 58—(2R)-2-Amino-5-guanidino-N-[(1R)-1-[(RS)-(5-ethyl-2-benzothiazolyl)hydroxymethyl]-3-methylbutyl]valeramide Trifluoroacetate This compound was prepared, as described in Compound 37, except the starting materials were [(1R)-1-[(RS)-(5-ethyl-2-benzothiazolyl)hydroxymethyl]-3-methyl-butylamine and N,N',N''-tri-Boc-arginine.

Compound 59—(2R)-2-Amino-5-guanidino-N-[(1R)-1-[(RS)-(5-cyclopropylmethy-2-benzothiazoly)hydroxymethyl]-3-phenylpropyl]valeramide Trifluoroacetate This compound was prepared, as described in Compound 37, except the starting materials were [(1R)-1-[(RS)-(5-cyclopropyhmethyl-2-benzthiazolyl)hydroxy-methyl]-3-phenylpropylamine and N,N',N''-tri-Boc-arginine.

Compound 60—(2R)-2,5Diamino-N-[(1R)-1-[(RS)-[5-(2,4-difluorophenylthio)-2-benzothiazolyl]hydroxymethyl]-3-(2-thienyl)propyl]valeramide Trifluoroacetate This compound was prepared, as described in Compound 37, except the starting materials were [(1R)-1-[(RS)-[5-(2,4-difluorophenylthio)-2-benzothiazolyl)hydroxy-methyl]-3-(2-thienyl)propylaniine and N,N'-bis-Boc-ornithine.

Compound 61—2-[(1R)-1-[[(2RS, 3R)-3,6-Diamino-2-hydroxyhexyl]amino]-3-phenyl-propyl]-N-(3-quinolyl)-4oxazolecarboxamide Trifluoroacetate (A) N,N'-Bis-Boc-(2RS, 3R)-3-Amino-2-hydroxypiperidine A suspension of N,N'-bis-Boc-D-ornithinol (804 mg), 4Å molecular sieves (1.6 g) and anhydrous dichloromethane (8 mL), under nitrogen atmosphere, is stirred for 20 min at 25° C. N-Methylmorpholine N-oxide (NMO, 596 mg) and tetrpropylammoni-um perruthenate (TPAP, 25 mg) are added and the reaction mixture is stirred at 25° C. After 4 h, additional NMO (200 mg) and TPAP (15 mg) was added and stirring continued for another hour. The reaction mixture was filtered, concentratrated in vacuo and purified by chromatography over silica gel (35% ethyl acetate/hexane) to afford titled product (492 mg) as a white solid. The two diastereomers are separable by flash chromatography. Diastereomer A: mass spectrum (ES+) m/e 339.2 (M+23 (Na)); $^1$H NMR (400 MHz, CDCl$_3$) δ1.51 (s, 9H), 1.56 (s, 1H), 1.59 (m, 1H), 1.87 (m, 1H), 2.01 (m, 1H), 2.24 (m, 1H), 3.12 (m, 1H), 3.55 (m, 1H), 3.82 (m, 1H), 3.87 (ma, 1H, OH), 4.77 (m, 1H, NH), and 5.58 (s, 1H). Diastereomer B: mass spectrum (ES+) m/e 339.2 (M+23 (Na)); $^1$H NMR (400 MHz, CDCl$_3$) δ1.49 (s, 18H), 1.61 (m, 2H), 1.72 (m, 1H), 1.90 (m, 1H), 2.98 (t, J=10.8 Hz, 1H), 3.63 (m, 1H), 3.78 (bd, J=11.7 Hz, 1H), 4.96 (m, 1H, NH), and 5.62 (s, 1H ).

(B) N,N'-Bis-Boc-(3R)-3,6-diaminohexene

A cold (0° C.) suspension of sodium hydride (864 mg of a 35% dispersion) in dry tetrahydrofuran (40 mL) and DMSO (8 mL), under nitrogen atmosphere, was treated dropwise with hexamethyldisilazane (1.6 mL) and stirred 1 h. The above mixture is added dropwise to a solution of methyltriphenylphosphonium bromide (2.7 g) in tetrahydrofiran (35 mL) at 0° C. After sting at 0° C. for 1.5 h, the mixture is cooled to −78° C. and N,N'-bis-Boc-(2RS, 3R)-amino-2-hydroxypiperidine (598 mg) in tetrahydroflran (9.5 mL) is added dropwise. The temperature is slowly raised to 40° C. and maintained for 12 h. The reaction is quenched with methanol (4 mL) and poured into a 10% aqueous solution of Rochelle salts (100 mL). Extraction with ethyl acetate, washing with water, drying ($Na_2SO_4$), concentration and flrther purification by chromatography over silica gel (10 to 35% ethyl acetate/hexane) afforded the olefin (530 mg) as a colorless oil: mass spectrum (ES+) mnle 337.3 (M+23 (Na)); $^1$H NMR (400 MHz, $CDCl_3$) δ1.49 (m, 23H), 3.16 (m, 2H), 4.04 (m, 1H), 4,55 (bs, 1H, NH), 4.63 (bs, 1H, NH), 5.06 (d, J=12.3 Hz, 1H), 5.16 (d, J=15.8 Hz, 1H), and 5.73 (m, 1H).

(C) N,N'-Bis-Boc-(3R)-3,6-diaminohexene oxide

A cold (0° C.) solution of N,N'-bis-Boc-(3R)-3,6-diaminohexene (0.95 g) in dichloromethane (30 mL), under nitrogen atmosphere, is treated with meta-chloroperbenzoic acid (2.61 g). The reaction mixture stirred at 25° C. for 12 h and diluted with ether. The organics were washed twice with 10% $Na_2S_2O_3$, 3 times with saturated aqueous bicarbonate, twice with brine, dried ($Na_2SO_4$), concentrated and purified flrther by chromatography over silica gel (30% ethyl acetate/hexane) to afford the desired epoxide (0.89 g) as a white solid: mass spectrum (ES+) m/e 353.1 (M+23 (Na)); $^1$H NMR (400 MHz, $CDCl_3$) δ1.44 (s, 18H), 1.60 (m, 4H), 2,59 (m, 1H), 2.76 (m, 1H), 3.00 (m, 1H), 3.19 (m, 2H), 3.91 (m, 1H), 5.42 (bs, 1H, NH), and 5.60 (bs, 1H, NH).

(D) 2-[(1R)-1-[[$N^3$, $N^6$-bis-Boc-(2RS, 3R)-3,6-diamino-2-hydroxyhexyl]amino]-3-phenylpropyl]-N-(3-quinolyl)-4-oxazolecarboxamide A mixture of 2-[(1R)-1-amino-3-phenylpropyl]-N-(3-quinolyl)-4-oxazole-carboxamide trifluoroacetate (112 mg), N,N'-bis-Boc-(3R)-3,6-diaminohexane epoxide (113 mg), anhydrous methanol (2.4 mL) and triethylamine (330 μL) was brought to reflux for 18 h. The reaction mixture is concentrated in vacuo and the residue is purified by chromatography over silica gel to afford the title compound (35 mg) as an oil: $^1$H NMR (400 MHz, $CDCl_3$) δ1.40 (s, 9H), 1.42 (s, 9H), 1.59 (m, 3H), 1.88 (m, 1H), 2.21 (m, 2H), 2.70 (m, 3H), 3.16 (m, 2H), 3.57 (m, 1H), 3.69 (m, 1H), 3.90 (m, 1H), 4.63 (m, 1H), 4.81 (m, 1H), 7.19 (m, 3H), 7.32 (m, 2H), 7.58 (t, J=8.6 Hz, 1H), 7.66(t, J=8.6 Hz, 1H), 7.85 (d, J=8.6 Hz, 1H), 8.09 (d, J=8.6 Hz, 1H), 8.31 (s, 1H), 8.93(s, 1H), 8.97 (bs, 1H, NH), 9.02 (s, 1H), and 9.13 (s, 1H, NH).

(E) 2-[(1R)-1-[[(2RS, 3R)-3,6-diamino-2-hydroxyhexyl] amino]-3-phenylpropyl]-N-(3-guinolyl)-4-oxazolecarboxamide Trifluoroacetate Deprotection (trifluoroacetic acid) of 2-[(1R)-1-[[$N^3$, $N^6$-bis-Boc-(2RS, 3R)-3,6-diamino-2-hydroxy-hexyl]amino]-3-phenylpropyl]-N-(3-quinolyl)-4-oxazolecarboxamide (29 mg) afforded the title compound (29 mg) as a white powder: $^1$H NMR (300 MHz, $D_2O$) δ1.83 (m, 4H), 2.64 (m, 1H), 2.78 (m, 2H), 2.78 (m, 2H), 3.11 (m, 2H), 3.25 (m, 1H), 3.40 (m, 2H), 4.22 (m, 1H), 4.81 (1H hidden under HOD peak), 7.22 (m, 3H), 7.38 (m, 2H), 8.01 (t, J=8.3 Hz, 1H), 8.18 (t, J=8.3 Hz, 1H), 8.26 (d, J=8.3 Hz, 1H), 8.34 (d, J=8.3 Hz, 1H), 8.66 (s, 1H), 9.23 (s, 1H), and 9.61 (s, 1H).

Compound 62—(2RS, 3R)-3,6-Diamino-1-[[(1R-1-[(RS)-(5,6-dimethyl-2-benzoxazolyl)hydroxymethyl]-3-phenylpropyl]amino]-2-hexanol Trifluoroacetate (A) $N^3$, $N^6$-Bis-Boc-(2RS, 3R)-3,6-Diamino-1-[[(1R)-1-[[(RS)-(5,6-dimethyl-2-benzoxazolyl)hydroxymethyl]-3-amino]-2-hexanol This compound is prepared from (1R)-1-[(RS)-(5,6-dimethyl-2-benzoxazolyl)-hydroxymethyl]-3-phenylpropylanine and N,N'-bis-Boc-(3R)-3,6-diaminohexene oxide to afford a clear oil: $^1$H NMR (400 MHz, $CDCl_3$, mixture of diastereomers) δ1.41–1.44 (2bs, 18H), 1.51 (m, 2H), 1.58 (m, 2H), 1.78 (m, 1H), ), 1.91 (m, 1H), 2.39 (m, 6H), 2.71 (m, 2H), 3.04 (m, 2H ), 3.57 (m, 1H), 3.63 (m, 1H), 3.84 (m, 4H), 4.84–5.09 (m, 1H), 7.10–7.36 (m, 6H), and 7.42 (s, 1H).

(B) (2RS, 3R)-3,6-Diamino-1-[[(1R)-1-[(RS)-(5,6-dimethyl-2-benzoxazolyl)hydroxy-methyl]-3-phenylpropyl]amino]-2-hexanol Trifluoroacetate Deprotection (trifluoroacetic acid) of $N^3$, $N^6$- bis-Boc-(2RS, 3R)-3,6-diamino-1-[[(1R)-1-[(RS)-5,6-dimethyl-2-benzoxazolyl)hydroxymethyl]-3-phenylpropyl]-amino]-2-hexanol (20 mg) afforded titled compound (20 mg) as a white powder: mass spectrum (ES+) m/e 441.3 (M+1); $^1$H NMR (300 MHz, $D_2O$, mixture of diastereomers) δ1.74 (m, 4H), 2.00–2.22 (m, 2H), 2.37 (m, 3H), 2.39 (s, 3H), 2.66 (m, 2H), 3.02 (m, 2H), 3.02 (m, 2H), 3.39 (m, 1H), 3.38 (m, 0.6H), 4.06 (m, 0.4H), 5.19 (d, J=5.0 Hz, 0.6H), 5.37 (s, 0.4H), 7.08–7.27 (m, 5H), 7.44 (2s, 2H), 7.48, 7.52, and 7.54.

Compound 63—(2RS, 3R)-3,6-Diamino-1-[[(1R)-1-[(RS)-(5-benzyl-2-benzoxazolyl)-hydroxymethyl]-3-phenylpropyl]amino]-2-hexanol Trifluoroacetate This compound was prepared, as described in Compound 62, except the starting materials were (1R-1-[(RS)-(5-benzyl-2-benzoxazolyl)hydroxymethyl]-3-phenyl-propylamine and N,N'-bis-Boc-(R)-3,6-diaminohexene oxide.

Compound 64—(2RS, 3R)-3,6-Diamino-1-(1R)1-[(RS)-(5,6-dichloro-2-benzoxazolyl)hydroxymethyl]-3-phenylpropyl]amino]-2-hexanol Trifluoroacetate This compound was prepared, as described in Compound 62, except the starting materials were (1R)-1-[(RS)-(5,6-dichloro-2-benzoxazolyl)hydroxymethyl]-3-phenylpropylamine and N,N'-bis-Boc-(RS)-3,6-diaminohexene oxide.

Compound 65—(2RS, 3R)-3,6-Diamino-1-[(1R)-1-[(RS)-(5-benzyl-2-benzothiazolyl)-hydroxymethyl]-3-phenylpropyl]amio-2-hexanol Trifluoroacetate This compound was prepared, as described in Compound 62, except the starting materials were (1R)-1-[(RS)-(5-benzyl-2-benzothiazolyl)hydroxymethyl]-3-phenyl-propylamine and N,N'-bis-Boc-(3R)-3,6-diaminohexene oxide.

Compound 66—(2RS, 3R)-3,5-Diamino-1-[[(1R)-1-(RS)-(1,5-dimethyl-2-benzimidazolyl)hydroxymethyl]-3methylbutyl]amino]-2-pentanol Trifluoroacetate This compound was prepared, as described in Compound 62, except the starting materials were (1R)-1-[(RS)-(1,5-dimethyl-2-benzimidazolyl)hydroxymethyl]-3-methylbutylamine and N,N'-bis-Boc-(3R)-3,5-diaminopntene oxide.

Compound 67—(2RS, 3R)-3,5-Diamino-1-[[(1R)-1-[(RS)-(5,6-dimethy-2-benzoxazolyl)hydroxymethyl]-3-phenylpropyl]amino]-2-pentanol Trifluoroacetate This compound was prepared, as described in Compound 62, except the starting materials were (1R)-1-[(RS)-(5,6-dimethyl-2-benzoxazolyl)hydroxymethyl]-3- phenylpropylamine and N,N'-bis-Boc-(3R)-3,5-diaminopentene oxide.

Compound 68—(2RS, 3R)-3,6-Diamino-1-[[(1R)-1-[(RS)-(5,6-dimethyl-2-benzoxazolyl)hydroxymethyl]-2-(3-thienyl)ethyl]amino]-2-hexanol Trifluoroacetate This compound was prepared, as described in Compound 62, except the starting materials were (1R)-1-[(RS)-(5,6-dimethyl-2-benzoxazolyl)hydroxymethyl]-2-(3-thienyl)ethylamnine and N,N'-bis-Boc-(3R)-3,6-diaminohexene oxide.

Compound 69—(2RS, 3R)-3,6-Diamino-1-[[(1R)-1-[(RS)-(5-phenoxy-2-benzimida-zolyl)hydroxymethyl]-3-(4-fluorophenyl)propyl]amino]-2-hexanol Trifluoroacetate This compound was prepared, as described in Compound 62, except the starting materials were (1R)-1-[(RS)-(5-phenoxy-2-benzimidazolyl)hydroxymethyl]-3-(4-fluorophenyl)-propylanmine and N,N'-bis-Boc-(3R)-3,6diaminohexene oxide.

All patents and publications mentioned in the specification are indicative of the levels of skill of those skilled in the art to which the invention pertains. All references cited in this disclosure are incorporated by reference to the same extent as if each reference had been incorporated by reference in its entirety individually. One skilled in the art would readily appreciate that the present invention is well adapted to carry out the objects and obtain the ends and advantages mentioned, as well as those inherent therein. The specific compounds and methods described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic description.

The invention illustratively described herein suitably may be practiced in the absence of any element or elements, limitation or limitations which is not specifically disclosed herein. Thus, for example, in each instance herein any of the terms "comprising," "comprising essentially of," and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in tenns of any individual member or subgroup of members of the Markush group or other group.

Thus, additional embodiments are within the scope of the invention and within the following claims.

What we claim is:

1. A method of enhancing the antimicrobial activity of an antimicrobial agent against a microbe, comprising contacting said microbe with said antimicrobial agent and an efflux pump inhibitor in an amount effective to inhibit an efflux pump in said microbe, wherein said efflux pump inhibitor has the chemical structure:

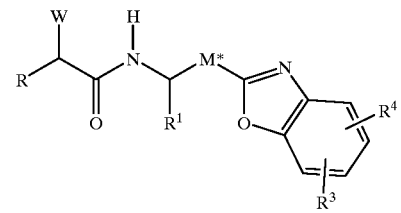

wherein;

M* is selected from the group consisting of $(CH_2)_n$, and CH(OH), wherein the carbon can have either R- or S-configuration, and wherein n is 0, 1, or 2;

R and $R^1$ are independently selected from the group consisting of H, lower alkyl, branched alkyl, fluoroalkyl, carboxyalkyl, hydroxyalkyl, alyl, 2-(or 3-)thienyl, 2-(or 3-)furyl, 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, and $(CH_2)_nN=C(H)NR^bR^c$, wherein n is 1, 2, 3, or 4;

$R^a$, $R^b$, and $R^c$ are independently selected from the group consisting of H, lower alkyl, phenyl, substituted phenyl, benzyl, cyano, hydroxyl, and nitro, or $R^a$ and $R^b$ or $R^b$ and $R^c$ taken together form a group selected from the group consisting of $(CH_2)_{2-3}$ and —CH=CH—;

$R^3$ and $R^4$ are independently selected from the group consisting of H, lower alkyl, branched alkyl, halogen, aryl, arylalkyl, thienylalkyl, furylalkyl, alkoxyl, alkylthio, aryloxy, and arylthio;

W is selected from the group consisting of amino, azaheterocycles, substituted azaheterocycles, hydroxyl, alkoxy, alkylthio, guanidino, and amidino; and where there are centers of asymmetry, the absolute stereochemistry can be either R or S- configuration or any combination of configurations.

2. The method of claim 1, wherein said efflux pump inhibitor has the structure:

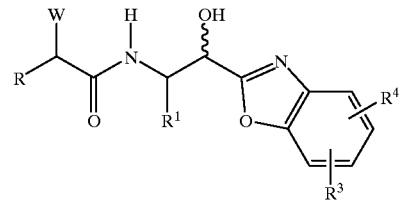

wherein:

R and $R^1$ are independently selected from the group consisting of H, lower alkyl, branched alkyl, fluoroalkyl, carboxyalkyl, hydroxyalkyl, aryl, mono-substituted aryl, disubstituted aryl, 2-(or 3-)thienyl, 2-(or 3-)furyl, 2-(3- or 4-)-pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)$ NR$^b$R$^c$, (CH$_2$)$_n$C=(NR$^a$)NR$^b$R$^c$, and (CH$_2$)$_n$N=C(H)NR$^b$R$^c$, wherein n is 1, 2, 3, or 4;

R$^a$, R$^b$, and R$^c$ are independently selected from the group consisting of H, lower alkyl, phenyl, benzyl, cyano, hydroxy, and nitro; or R$^a$ and R$^b$ or R$^b$ and R$^c$ taken together form a group selected from the group consisting of (CH$_2$)$_{2-3}$ and —CH=CH—;

R$^3$ and R$^4$ are independently selected from the group consisting of H, lower alkyl, branched alkyl, halogen, aryl, arylalkyl thienylalkyl, furylalkyl, alkoxyl, alkylthio, aryloxy, and arylthio;

W is selected from the group consisting of amino, azaheterocycles, substituted azaheterocycles, hydroxy, alkoxy, alkylthio, guanidino, and amidino; and where there are centers of asymmetry, the absolute stereochemistry can be either R or S- configuration or any combination of configurations.

3. The method of claim 1, wherein said microbe is a bacterium.

4. The method of claim 3, wherein said bacterial infection involves a bacterium selected from the group consisting of Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Yibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, Staphylococcus saccharolyticus.

5. The method of claim 1, wherein said microbial infection is a bacterial infection and said antimicrobial agent is an antibacterial agent.

6. The method of claim 5, wherein said antibacterial agent is a quinolone.

7. The method of claim 5, wherein said antibacterial agent is a tetracycline.

8. The method of claim 5, wherein said antibacterial agent is a β-lactam.

9. The method of claim 5, wherein said antibacterial agent is a coumermycin.

10. The method of claim 5, wherein said antibacterial agent is chloranphenicol.

11. The method of claim 5, wherein said antibacterial agent is a glycopeptide.

12. The method of claim 5, wherein said antibacterial agent is an aminoglycoside.

13. The method of claim 5, wherein said antibacterial agent is a macrolide.

14. The method of claim 5, wherein said antibacterial agent is a rifamycin.

15. The method of claim 5, wherein said antibacterial agent is an oxazolidonone.

16. The method of claim 1, wherein said antimicrobial agent is effluxed by a microbe.

17. A pharmaceutical composition effective for treatment of an infection of an animal by a microbe, comprising an efflux pump inhibitor, an antimicrobial agent and a pharmaceutically acceptable carrier, wherein said efflux pump inhibitor has the chemical structure:

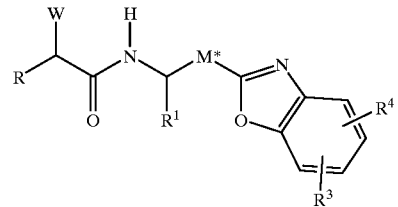

wherein:

M* is selected from the group consisting of (CH$_2$)$_n$, and CH(OH), wherein the carbon can have either R- or S-configuration, and wherein n is 0, 1, or 2;

R and R$^1$ are independently selected from the group consisting of H, lower alkyl, branched alkyl, fluoroallyl, carboxyalkyl, hydroxyalkyl, aryl, 2-(or 3-)thienyl, 2-(or 3-)furyl, 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, and (CH$_2$)$_n$N=C(H)NR$^b$R$^c$, wherein n is 1, 2, 3, or 4;

R$^a$, R$^b$, and R$^c$ are independently selected from the group consisting of H, lower alkyl, phenyl, substituted phenyl, benzyl, cyano, hydroxyl, and nitro, or R$^a$ and R$^b$ or R$^b$ and R$^c$ taken together form a group selected from the group consisting of (CH$_2$)$_{2-3}$ and —CH=CH—;

R$^3$ and R$^4$ are independently selected from the group consisting of H, lower alkyl, branched alkyl, halogen, aryl, arylalkyl, thienylalkyl, furylalkyl, alkoxyl, alkylthio, aryloxy, and arylthio;

W is selected from the group consisting of amino, azaheterocycles, substituted azaheterocycles, hydroxyl, alkoxy, alkylthio, guanidino, and amidino; and where there are centers of asymmetry, the absolute stereochemistry can be either R or S- configuration or any combination of configurations.

18. The pharmaceutical composition of claim 17, wherein said efflux pump inhibitor has the structure:

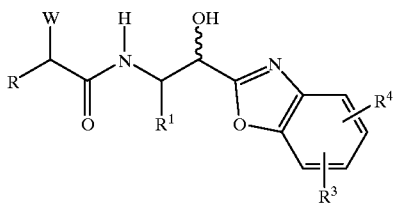

wherein:
- R and R¹ are independently selected from the group consisting of H, lower alkyl, branched alkyl, fluoroalkyl, carboxyalkyl, hydroxyalkcyl, aryl, mono-substituted aryl, disubstituted aryl, 2-(or 3-)thienyl, 2-(or 3-)furyl, 2-(3- or 4-)-pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, and $(CH_2)_nN=C(H)NR^bR^c$, wherein n is 1, 2, 3, or 4;
- $R^a$, $R^b$, and $R^c$ are independently selected from the group consisting of H, lower alkyl, phenyl, benzyl, cyano, hydroxy, and nitro; or $R^a$ and $R^b$ or $R^b$ and $R^c$ taken together form a group selected from the group consisting of $(CH_2)_{2-3}$ and —CH=CH—;
- R³ and R⁴ are independently selected from the group consisting of H, lower alkyl, branched alkyl, halogen, aryl, arylalkyl, thienylalkyl, furylalkyl, alkoxyl, alkylthio, aryloxy, and arylthio;
- W is selected from the group consisting of amino, azaheterocycles, substituted azaheterocycles, hydroxy, alkoxy, alkylthio, guanidino, and amidino; and
- where there are centers of asymmetry, the absolute stereochemistry can be either R or S- configuration or any combination of configurations.

19. A method of suppressing growth of a bacterium expressing an efflux pump, comprising contacting said bacterium with an efflux pump inhibitor in the presence of a concentration of antibacterial agent below the MIC of said bacterium, wherein said efflux pump inhibitor has the chemical structure:

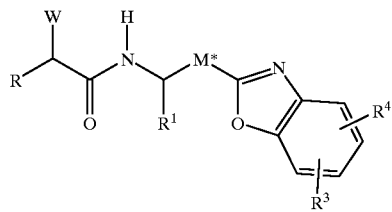

wherein:
M* is selected from the group consisting of $(CH_2)_n$, and CH(OH), wherein the carbon can have either R- or S-configuration, and wherein n is 0, 1, or 2;
- R and R¹ are independently selected from the group consisting of H, lower alkyl, branched alkyl, fluoroalkyl, carboxyalkyl, hydroxyalkyl, aryl, 2-(or 3-)thienyl, 2-(or 3-)furyl, 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, and $(CH_2)_nN=C(H)NR^bR^c$, wherein n is 1, 2, 3, or 4;
- $R^a$, $R^b$, and $R^c$ are independently selected from the group consisting of H, lower alkyl, phenyl, substituted phenyl, benzyl, cyano, hydroxyl, and nitro, or $R^a$ and $R^b$ or $R^b$ and $R^c$ taken together form a group selected from the group consisting of $(CH_2)_{2-3}$ and —CH=CH—;
- R³ and R⁴ are independently selected from the group consisting of H, lower alkyl, branched alkyl, halogen, aryl, arylalkyl, thienylalkyl, furylalkyl, alkoxyl, alkylthio, aryloxy, and arylthio;
- W is selected from the group consisting of amino, azaheterocycles, substituted azaheterocycles, hydroxyl, alkoxy, alkyltho, guanidino, and amidino; and
- where there are centers of asymmetry, the absolute stereochemistry can be either R or S- configuration or any combination of configurations.

20. The method of claim 19, wherein said efflux pump inhibitor has the structure:

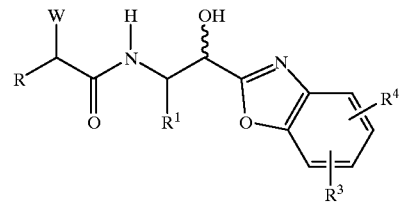

wherein:
- R and R¹ are independently selected from the group consisting of H, lower alkyl, branched alkyl, fluoroalkyl, carboxyalkyl, hydroxyalkyl, aryl, mono-substituted aryl, disubstituted aryl, 2-(or 3-)thienyl, 2-(or 3-)furyl, 2-(3- or 4-)-pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, and $(CH_2)_nN=C(H)NR^bR^c$, wherein n is 1, 2, 3, or 4;
- $R^a$, $R^b$, and $R^c$ are independently selected from the group consisting of H, lower alkyl, phenyl, benzyl, cyano, hydroxy, and nitro; or $R^a$ and $R^b$ or $R^b$ and $R^c$ taken together form a group consisting of $(CH_2)_{2-3}$ and —CH=CH—;
- R³ and R⁴ are independently selected from the group consisting of H, lower alkyl, branched alkyl, halogen, aryl, arylalkyl, thienylalkyl, furylalkyl, alkoxyl, alkylthio, aryloxy, and arylthio;
- W is selected from the group consisting of amino, azaheterocycles, substituted azaheterocycles, hydroxy, alkoxy, alkylthio, guanidino, and amidino; and
- where there are centers of asymmetry, the absolute stereochemistry can be either R or S- configuration or any combination of configurations.

21. An efflux pump inhibitor compound, wherein said compound has the chemical structure:

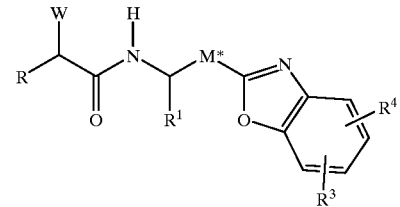

wherein:
M* is selected from the group consisting of $(CH_2)_N$, and CH(OH), wherein the carbon can have either R- or S-configuration, and wherein n is 0, 1, or 2;

R and R¹ are independently selected from the group consisting of H, lower alkyl, branched alkyl, fluoroalkyl, carboxyalkyl, hydroxyalkyl, aryl, 2-(or 3-)thienyl, 2-(or 3-)furyl, 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, and $(CH_2)_nN=C(H)NR^bR^c$, wherein n is 1, 2, 3, or 4;

$R^a$, $R^b$, and $R^c$ are independently selected from the group consisting of H, lower alkyl, phenyl, substituted phenyl, benzyl, cyano, hydroxyl, and nitro, or $R^a$ and $R^b$ or $R^b$ and $R^c$ taken together form a group selected from the group consisting of $(CH_2)_{2-3}$ and —CH=CH—;

R³ and R⁴ are independently selected from the group consisting of H, lower alkyl, branched alkyl, halogen, aryl, arylalkyl, thienylalkyl, furylalkyl, alkoxyl, alkylthio, aryloxy, and arylthio;

W is selected from the group consisting of amino, azaheterocycles, substituted azaheterocycles, hydroxyl, alkoxy, alkylthio, guanidino, and amidino; and where there are centers of asymmetry, the absolute stereochemistry can be either R or S- configuration or any combination of configurations.

22. The efflux pump inhibitor compound of claim 21, wherein said compound has the chemical structure:

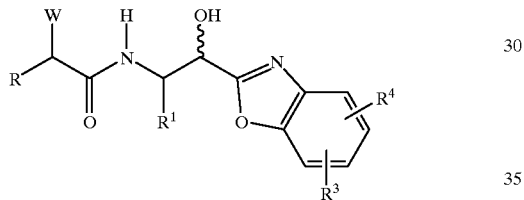

wherein:

R and R¹ are independently selected from the group consisting of H, lower alkyl, branched alkyl, fluoroalkyl, carboxyalkyl, hydroxyalkyl, aryl, mono-substituted aryl, disubstituted aryl, 2-(or 3-)thienyl, 2-(or 3-)furyl, 2-(3- or 4-)-pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, and $(CH_2)_nN=C(H)NR^bR^c$, wherein n is 1, 2, 3, or 4;

$R^a$, $R^b$, and $R^c$ are independently selected from the group consisting of H, lower alkyl, phenyl, benzyl, cyano, hydroxy, and nitro; or $R^a$ and $R^b$ or $R^b$ and $R^c$ taken together form a group selected from the group consisting of $(CH_2)_{2-3}$ and —CH=CH—;

R³ and R⁴ are independently selected from the group consisting of H, lower alkyl, branched alkyl, halogen, aryl, arylalkyl, thienylalkyl, furylalkyl, alkoxyl, alkylthio, aryloxy, and arylthio;

W is selected from the group consisting of amino, azaheterocycles, substituted azaheterocycles, hydroxy, alkoxy, alkylthio, guanidino, and amidino; and where there are centers of asymmetry, the absolute stereochemistry can be either R or S- configuration or any combination of configurations.

* * * * *